US011335000B2

(12) United States Patent
Iwata et al.

(10) Patent No.: US 11,335,000 B2
(45) Date of Patent: May 17, 2022

(54) FERTILE OVUM QUALITY EVALUATION METHOD, FERTILE OVUM QUALITY EVALUATION SYSTEM, PROGRAM, AND INFORMATION PROCESSING APPARATUS

(71) Applicant: Sony Corporation, Tokyo (JP)

(72) Inventors: Mina Iwata, Tokyo (JP); Masataka Shinoda, Kanagawa (JP)

(73) Assignee: Sony Corporation, Tokyo (JP)

( * ) Notice: Subject to any disclaimer, the term of this patent is extended or adjusted under 35 U.S.C. 154(b) by 65 days.

(21) Appl. No.: 16/757,362

(22) PCT Filed: Oct. 15, 2018

(86) PCT No.: PCT/JP2018/038248
§ 371 (c)(1),
(2) Date: Apr. 17, 2020

(87) PCT Pub. No.: WO2019/082713
PCT Pub. Date: May 2, 2019

(65) Prior Publication Data
US 2020/0349709 A1   Nov. 5, 2020

(30) Foreign Application Priority Data

Oct. 26, 2017   (JP) .............................. JP2017-207293

(51) Int. Cl.
*G06K 9/00* (2022.01)
*G06T 7/00* (2017.01)
(Continued)

(52) U.S. Cl.
CPC ............ *G06T 7/0016* (2013.01); *A01K 67/00* (2013.01); *G06T 7/13* (2017.01); *G06T 7/62* (2017.01);
(Continued)

(58) Field of Classification Search
CPC .................................................. G06T 7/0016
See application file for complete search history.

(56) References Cited

U.S. PATENT DOCUMENTS 10,510,143 B1 * 12/2019 Zhou ..................... G06T 7/0012
2010/0195877 A1   8/2010 Oonishi et al.
(Continued)

FOREIGN PATENT DOCUMENTS

JP         H07-170885 A       7/1995
JP         2010-181402 A      8/2010
(Continued)

OTHER PUBLICATIONS

International Search Report and Written Opinion dated Jan. 2, 2019 in connection with International Application No. PCT/JP2018/038248.
(Continued)

*Primary Examiner* — Oneal R Mistry
(74) *Attorney, Agent, or Firm* — Wolf, Greenfield & Sacks, P.C.

(57) ABSTRACT

There is provided a computer system for evaluating the quality of a fertile ovum. The computer system includes computer processing circuitry configured to receive a plurality of images of a fertile ovum captured in time-series by an imaging apparatus, provide as input to at least one learned model, the plurality of images of the fertile ovum or information based on the plurality of images of the fertile ovum, wherein the at least one learned model has been trained to output, based at least in part, on the plurality of images, fertile ovum analysis information describing characteristics of the fertile ovum used to evaluate a quality of fertile ovum, and provide evaluation support information based, at least in part, on the fertile ovum analysis information, wherein the evaluation support information enables a quality evaluator to interact with the web dashboard to modify at least some of the evaluation support information.

21 Claims, 23 Drawing Sheets

(51) Int. Cl.
*G06T 7/62* (2017.01)
*G06T 7/13* (2017.01)
*G16H 50/20* (2018.01)
*G16H 30/40* (2018.01)
*A01K 67/00* (2006.01)
*A61D 19/04* (2006.01)

(52) U.S. Cl.
CPC ............ *G16H 30/40* (2018.01); *G16H 50/20* (2018.01); *A61D 19/04* (2013.01); *G06T 2207/20081* (2013.01); *G06T 2207/30024* (2013.01); *G06T 2207/30044* (2013.01)

(56) References Cited

U.S. PATENT DOCUMENTS

2014/0220618 A1* 8/2014 Wirka ................ G06K 9/00134
435/34
2014/0247972 A1 9/2014 Wang et al.

FOREIGN PATENT DOCUMENTS

| JP | 2011072263 A | 4/2011 |
| JP | 2016-509844 A | 4/2016 |
| JP | 2016509845 A | 4/2016 |
| WO | 2012/002500 A1 | 1/2012 |
| WO | 2014/134527 A1 | 9/2014 |
| WO | 2014/134550 A1 | 9/2014 |

OTHER PUBLICATIONS

International Preliminary Report on Patentability dated May 7, 2020 in connection with International Application No. PCT/JP2018/038248.

Chicken embryo development detection using Self-Organizing Maps and K-mean Clustering, Wisit Lumchanow, et al., 5th International Electrical Engineering Congress, 2017年3月10日.

Inner cell mass segmentation in human HMC embryo images using fully convolutional network, S. Kheradmand, et al., 2017 IEEE International Conference on Image Processing (ICIP), pp. 1752-1756, 2017年9月20日.

* cited by examiner

FERTILE OVUM QUALITY EVALUATION METHOD, FERTILE OVUM QUALITY EVALUATION SYSTEM, PROGRAM, AND INFORMATION PROCESSING APPARATUS

CROSS REFERENCE TO RELATED APPLICATIONS

This application claims the benefit under 35 U.S.C. § 371 as a U.S. National Stage Entry of International Application No. PCT/JP2018/038248, filed in the Japanese Patent Office as a Receiving Office on Oct. 15, 2018, which claims priority to Japanese Patent Application Number JP2017-207293, filed in the Japanese Patent Office on Oct. 26, 2017, each of which is hereby incorporated by reference in its entirety.

TECHNICAL FIELD

Cross Reference to Related Applications

This application claims the benefit of Japanese Priority Patent Application JP 2017-207293 filed Oct. 26, 2017, the entire contents of which are incorporated herein by reference.

The present technology, for example, relates to a fertile ovum quality evaluation method, a fertile ovum quality evaluation system, a program, and an information processing apparatus, in which a quality evaluation result of a cell such as a fertile ovum can be provided.

BACKGROUND ART

In the related art, for example, in the livestock industry treating livestock, a process of collecting a plurality of fertile ova from a uterus of a cow, of identifying normal fertile ova from the plurality of fertile ova, and of transplanting the fertile ova into a uterus of a cow different from the cow from which the fertile ova are collected, is performed several times (for example, PTL 1). At this time, the people working on site are greatly interested in the quality of the fertile ovum, which is an important factor of affecting a transplant record after the transplant.

CITATION LIST

Patent Literature

PTL 1: Japanese Patent Application Laid-open No. 07-170885

SUMMARY

Technical Problem

It is general that the quality of the fertile ovum is determined according to morphological findings using an optical microscope, an image processing apparatus, or the like. However, in quality evaluation of the fertile ovum before the transplant, a morphological evaluation method as described above tends not only to be skilled, but also to be easily subjective. For this reason, recently, it has been desirable to acquire a quality evaluation result of the fertile ovum evaluated with a higher degree of accuracy compared to the morphological findings, in order to select a good fertile ovum.

In consideration of the circumstances as described above, an object of the present technology is to provide a fertile ovum quality evaluation method, a fertile ovum quality evaluation system, a program, and an information processing apparatus, in which a quality evaluation result of a fertile ovum evaluated with a high degree of accuracy can be obtained.

Solution to Problem

According to the present disclosure, there is provided a computer system for evaluating the quality of a fertile ovum, the computer system including: computer processing circuitry configured to: receive a plurality of images of a fertile ovum captured in time-series by an imaging apparatus; provide as input to at least one learned model, the plurality of images of the fertile ovum or information based on the plurality of images of the fertile ovum, wherein the at least one learned model has been trained to output, based at least in part, on the plurality of images, fertile ovum analysis information describing characteristics of the fertile ovum used to evaluate a quality of fertile ovum; and provide, on a web dashboard provided in a web browser, evaluation support information based, at least in part, on the fertile ovum analysis information, wherein the evaluation support information enables a quality evaluator to interact with the web dashboard to modify at least some of the evaluation support information.

According to the present disclosure, there is provided a computer-implemented method for analyzing time series images of a fertile ovum, the method including: receiving, from an imaging apparatus, a plurality of images of a fertile ovum captured in time-series; providing as input to at least one learned model, the plurality of images of the fertile ovum or information based on the plurality of images, wherein the at least one learned model has been trained to output, based at least in part, on the plurality of images, fertile ovum analysis information describing characteristics of the fertile ovum used to evaluate a quality of fertile ovum; and displaying, on a web dashboard provided in a web browser, evaluation support information based, at least in part, on the fertile ovum analysis information, wherein the evaluation support information enables a quality evaluator to interact with the web dashboard to modify at least some of the evaluation support information.

According to the present disclosure, there is provided a non-transitory computer readable medium encoded with a plurality of instructions that, when executed by computer processing circuitry, perform a method including: receiving, from an imaging apparatus, a plurality of images of a fertile ovum captured in time-series; providing as input to at least one learned model, the plurality of images of the fertile ovum or information based on the plurality of images, wherein the at least one learned model has been trained to output, based at least in part, on the plurality of images, fertile ovum analysis information describing characteristics of the fertile ovum used to evaluate a quality of fertile ovum; and displaying, on a web dashboard provided in a web browser, evaluation support information based, at least in part, on the fertile ovum analysis information, wherein the evaluation support information enables a quality evaluator to interact with the web dashboard to modify at least some of the evaluation support information.

According to the present disclosure, there is provided a computer system for evaluating the quality of a fertile ovum, the computer system including: computer processing circuitry configured to: receive a plurality of images of a fertile ovum captured in time-series by an imaging apparatus; provide as input to at least one learned model, the plurality of images of the fertile ovum or information based on the plurality of images of the fertile ovum, wherein the at least one learned model has been trained to output, based at least in part, on the plurality of images, fertile ovum analysis information describing characteristics of the fertile ovum used to evaluate a quality of fertile ovum; and provide, on a web dashboard provided in a web browser, evaluation support information based, at least in part, on the fertile ovum analysis information, wherein the evaluation support information enables a quality evaluator to interact with the web dashboard to input quality information of the fertile ovum.

According to the present disclosure, there is provided an imaging processing system for evaluating the quality of a fertile ovum, the image processing system including: an imaging device configured to capture a time-series of images of a fertile ovum, wherein at least a part of the images in the time-series correspond to different developmental stages of the fertile ovum; a communications interface configured to connect via at least one network to at least one computer; and at least one storage medium configured to store a plurality of instructions received via the communications interface, wherein the plurality of instructions, when executed by computer processing circuitry, cause the computer processing circuitry to: control capturing of the time-series of images by the imaging device; provide the time-series of images or information based on the time-series of images to at least one learned model, wherein the at least one learned model has been trained to output, based at least in part, on the time-series of images, fertile ovum analysis information describing characteristics of the fertile ovum used to evaluate a quality of fertile ovum; and provide, on a web dashboard provided in a web browser, evaluation support information based, at least in part, on the fertile ovum analysis information, wherein the evaluation support information enables a quality evaluator to interact with the web dashboard to input quality information of the fertile ovum.

According to the present disclosure, there is provided an imaging processing system for evaluating the quality of a fertile ovum, the image processing system including: an imaging device configured to capture a time-series of images of a fertile ovum, wherein at least a part of the images in the time-series correspond to different developmental stages of the fertile ovum; a communications interface configured to connect via at least one network to at least one computer; and at least one storage medium configured to store a plurality of instructions received via the communications interface, wherein the plurality of instructions, when executed by computer processing circuitry, cause the computer processing circuitry to: provide the time-series of images or information based on the time-series of images to at least one learned model, wherein the at least one learned model has been trained to output, based at least in part, on the time-series of images, fertile ovum analysis information describing characteristics of the fertile ovum used to evaluate a quality of fertile ovum; and provide, on a web dashboard provided in a web browser, evaluation support information based, at least in part, on the fertile ovum analysis information, wherein the evaluation support information enables a quality evaluator to interact with the web dashboard to input quality information of the fertile ovum.

According to the present disclosure, there is provided an imaging processing system for evaluating the quality of a fertile ovum, the image processing system including: at least one storage medium configured to store a plurality of instructions that, when executed by computer processing circuitry, cause the computer processing circuitry to: provide a time-series of images captured by an imaging device or information based on the time-series of images to at least one learned model, wherein the at least one learned model has been trained to output, based at least in part, on the time-series of images, fertile ovum analysis information describing characteristics of the fertile ovum used to evaluate a quality of fertile ovum; and provide, on a web dashboard provided in a web browser, evaluation support information based, at least in part, on the fertile ovum analysis information, wherein the evaluation support information enables a quality evaluator to interact with the web dashboard to input quality information of the fertile ovum.

Advantageous Effects

As described above, according to the present technology, it is possible to provide a fertile ovum quality evaluation method, a fertile ovum quality evaluation system, a program, and an information processing apparatus, in which a quality evaluation result of a fertile ovum evaluated with a high degree of accuracy can be obtained. Note that the effects described above are not necessarily limited, and any effects described herein or other effects which can be grasped from the description described herein may be obtained along with the effects described above or instead of the effects described above.

DESCRIPTION OF EMBODIMENTS

Hereinafter, embodiments of the present technology will be described with reference to the drawings.

A fertile ovum quality evaluation system according to the present technology is a network system which is capable of mutually acquiring quality evaluation information of a fertile ovum evaluated with a high degree of accuracy in a fertile ovum manager, a fertile ovum quality evaluator, and a fertile ovum transplanter, through a network such as the internet.

Here, in the present technology, the fertile ovum manager, for example, is a production operator who cultures and manages a fertile ovum of livestock in a case of treating the fertile ovum of the livestock such as cattle, and corresponds to human reproductive clinic, a hospital, or the like which cultures and manages a human fertile ovum of a person in a case of treating the human fertile ovum.

The production operator, for example, corresponds to communities such as domestic and international companies or cooperative associations, which manage a culture environment or the like for culturing a fertile ovum, or various research institutions such as universities.

The fertile ovum quality evaluator, for example, corresponds to an embryologist or a staff aiding the embryologist, a farm producer who belongs to a production operator, and produces a fertile ovum, a medical doctor or a staff belonging to a human reproductive clinic or a hospital, or the like.

The fertile ovum transplanter, for example, is a farmer who glows a fertile ovum of livestock to an imago, and sells the imago to a market, in a case of treating the fertile ovum of the livestock such as cattle, and a breeder of an aggregate or the like of a plurality of farmers (for example, an agricultural cooperative or the like), and corresponds to a clinic, a hospital, or the like which transplants a human fertile ovum for a fertilization treatment in a case of treating the human fertile ovum. Hereinafter, the details of the fertile ovum quality evaluation system using the fertile ovum of the livestock such as cattle, as a target, will be described.

First Embodiment

<Outline of Fertile Ovum Quality Evaluation System>

Figure 1:
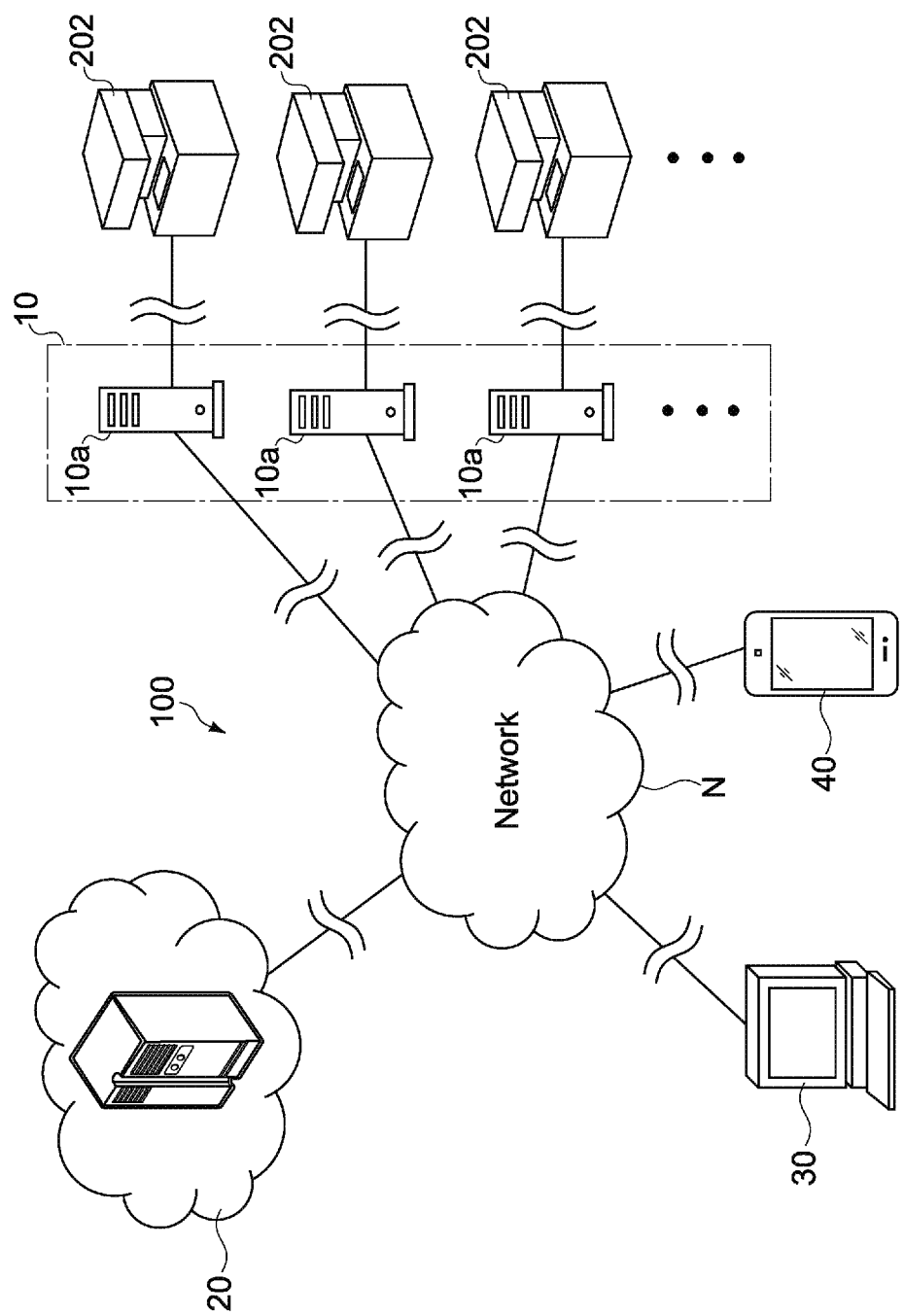
FIG. 1 is a schematic view schematically illustrating a configuration example of a fertile ovum quality evaluation system according to the present technology.

FIG. 1 is a schematic view schematically illustrating a configuration example of a fertile ovum quality evaluation system 100 according to this embodiment. As illustrated in FIG. 1, the fertile ovum quality evaluation system 100 includes a terminal device 10, an information processing apparatus 20, a first terminal 30, and a second terminal 40.

In this embodiment, the terminal device 10, the information processing apparatus 20, the first terminal 30, and the second terminal 40 are connected to each other through a network N such that communication can be performed with each other. The network N, for example, may be the internet or a mobile communication network, a local area network, or the like, or may be a network in which a plurality of types of networks are combined.

(Terminal Device)

Figure 2:
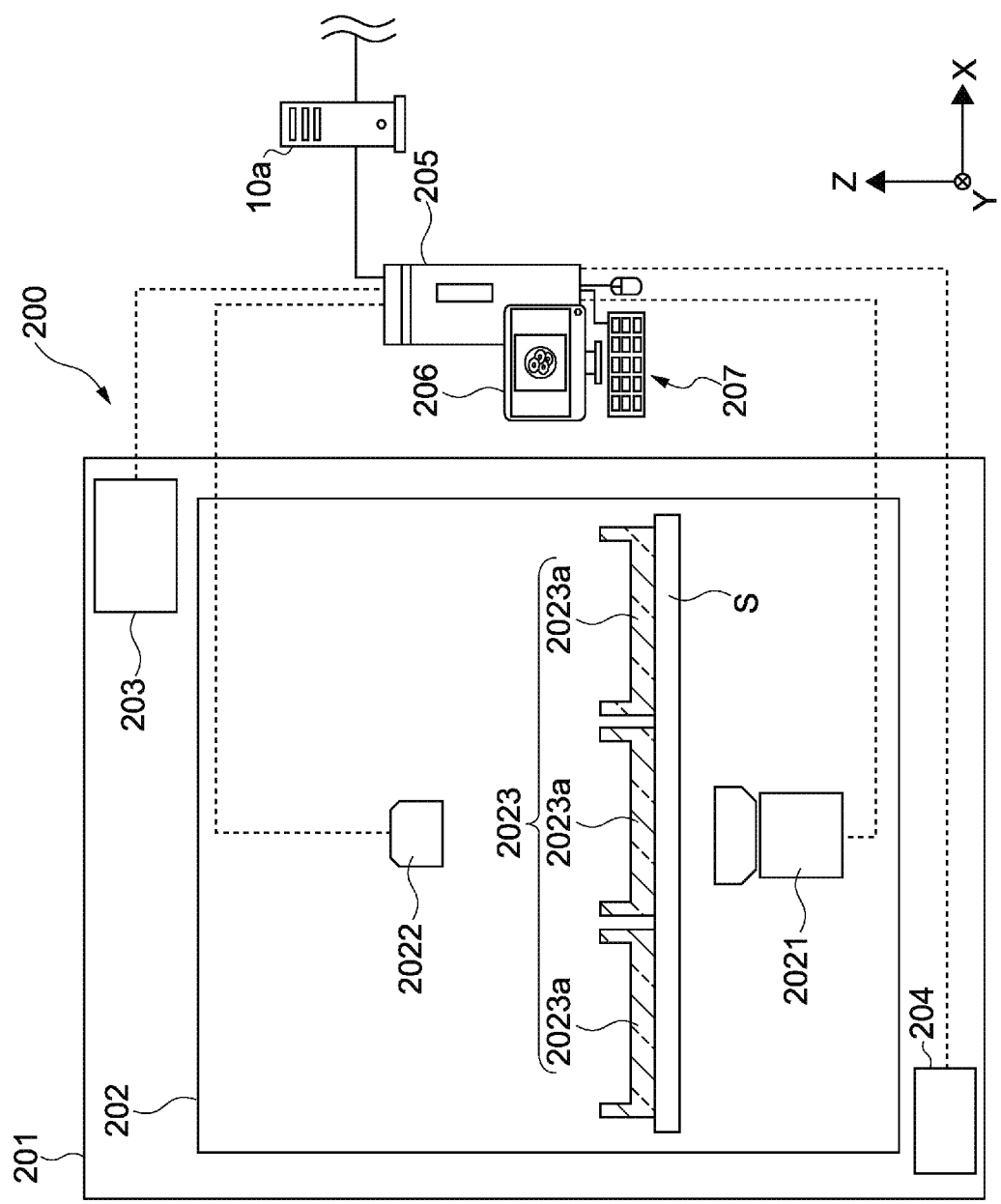
FIG. 2 is a schematic view of a configuration example of an observation system of the present technology.

As illustrated in FIG. 1, the terminal device 10 is configured of a plurality of gateway terminals 10a, and each of the gateway terminals 10a is connected to an observation device 202 (the fertile ovum manager) in a wireless manner or a wired manner, through a control recording PC 205 (refer to FIG. 2). The observation device 202 of this embodiment is handled by the fertile ovum manager.

Note that in the fertile ovum quality evaluation system 100 of this embodiment, typically, as illustrated in FIG. 1, a plurality of observation devices 202 (the fertile ovum manager) are connected to the information processing apparatus 20 through the terminal device 10, but the configuration is not limited thereto, and a single observation device 202 (the fertile ovum manager) may be connected to the information processing apparatus 20 through the terminal device 10.

(Observation System)

FIG. 2 is a schematic view of a configuration example of an observation system 200 including the observation device 202 of this embodiment. Note that an X axis, a Y axis, and a Z axis, illustrated in FIG. 2, are 3-axis directions orthogonal to each other, and the same applies to the following drawings.

As illustrated in FIG. 2, the observation system 200 includes an incubator 201, the observation device 202, a humidity?temperature?gas control unit 203, a detection unit 204, a control recording PC 205, a display device 206, and an input unit 207.

The incubator 201 is a culture device containing the observation device 202, the humidity?temperature?gas control unit 203, and the detection unit 204, and has a function of keeping the temperature, the humidity, or the like in the incubator 201 constant. The incubator 201 is configured such that arbitrary gas is capable of flowing into the incubator 201. The type of gas is not particularly limited, and for example, is nitrogen, oxygen, carbon dioxide, and the like.

The observation device 202 includes a capturing unit 2021, a light source 2022, and a culture dish group 2023. The capturing unit 2021 is capable of capturing fertile ova F (refer to FIG. 4) contained in a culture dish 2023a (a dish) in chronological order, and of generating observation images of the fertile ova F.

The capturing unit 2021 includes a lens barrel including a lens group movable in an optical axis direction (a Z axis direction), a solid capturing element capturing subject light passing through the lens barrel, such as a complementary metal oxide semi-conductor (CMOS) and a charge coupled device (CCD), a driving circuit driving such components, and the like.

The capturing unit 2021 can be moved in the optical axis direction (the Z axis direction) and a horizontal direction (a direction orthogonal to the Z axis direction), and captures the fertile ovum F contained in the culture dish 2023a while being moved in the horizontal direction. In addition, the capturing unit 2021 is capable of imaging not only a still image, but also a moving image.

The capturing unit 2021 according to this embodiment, typically, is a visible light camera, but is not limited thereto, and may be an infrared ray (IR) camera, a polarization camera, or the like.

The light source 2022 emits light with respect to the culture dish 2023a at the time of capturing the fertile ovum F in the culture dish 2023a with the capturing unit 2021. For example, a light emitting diode (LED) emitting light having a specific wavelength, or the like is adopted to the light source 2022. In a case where the light source 2022 is the LED, for example, a red LED emitting light having a wavelength of 640 nm is adopted.

The culture dish group 2023 is configured of a plurality of culture dishes 2023a, and is mounted on an observation stage S, between the capturing unit 2021 and the light source 2022. The observation stage S is capable of transmitting the light emitted from the light source 2022.

Figure 3:
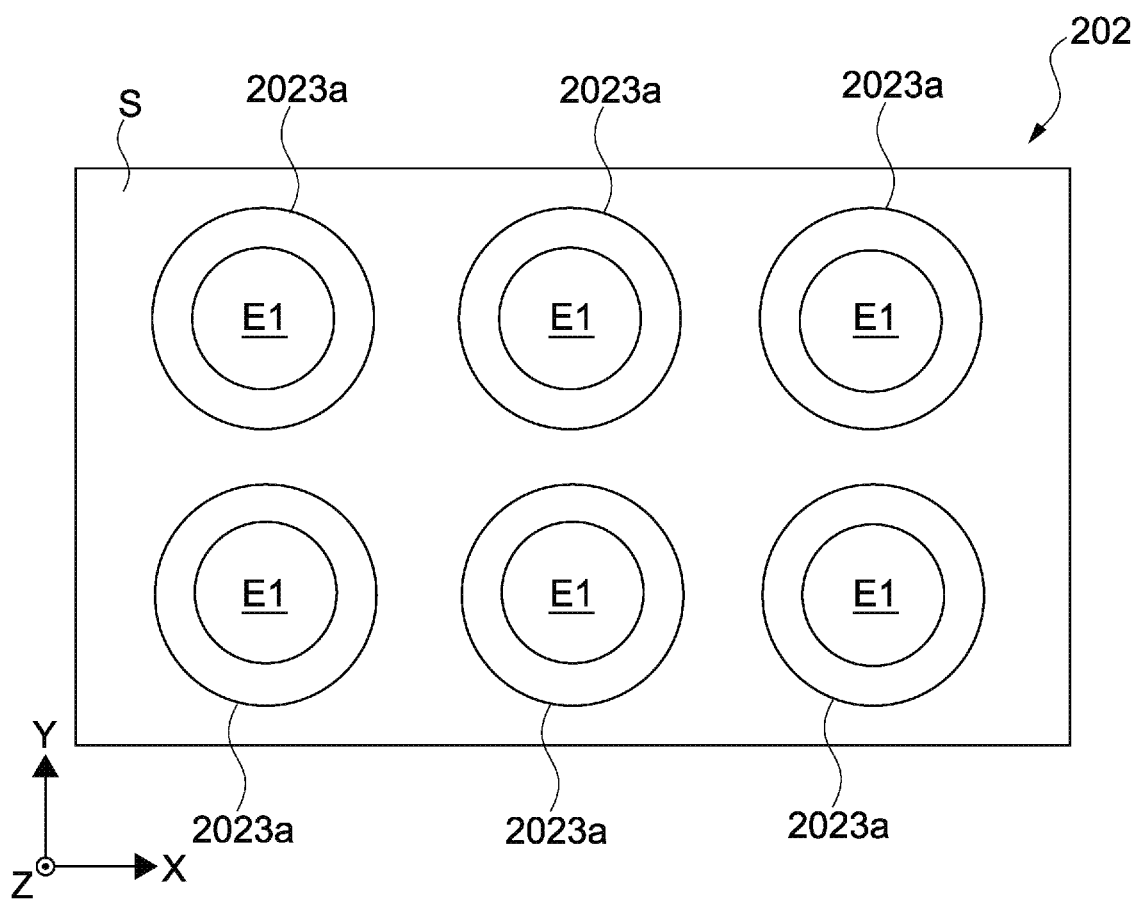
FIG. 3 is a schematic view of a culture dish group mounted on an observation stage of an observation device of the present technology seen from a light source side.

FIG. 3 is a schematic view of the culture dish group 2023 mounted on the observation stage S of the observation device 202 seen from the light source 2022 side. As illustrated in FIG. 3, for example, six culture dishes 2023a are mounted on the observation stage S into the shape of a matrix, three culture dishes 2023a are mounted in an X axis direction, and two culture dishes 2023a are mounted in a Y axis direction.

Figure 4:
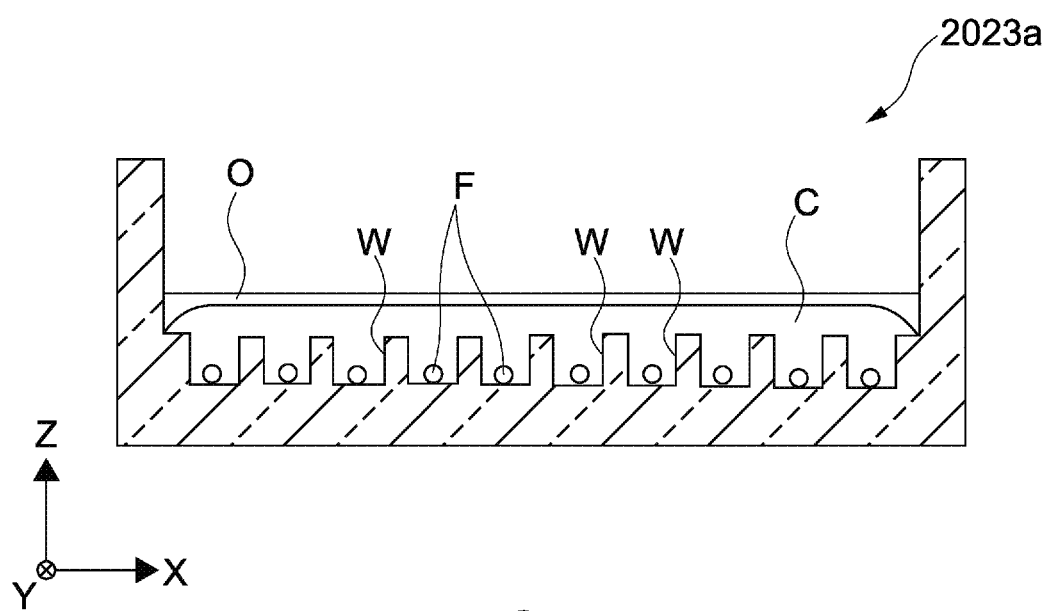
FIG. 4 is a diagram schematically illustrating a sectional surface of the culture dish.

FIG. 4 is a diagram schematically illustrating a sectional surface of the culture dish 2023a. As illustrated in FIG. 4, a plurality of wells W are provided in the culture dish 2023a. The wells W are provided in the culture dish 2023a into the shape of a matrix (refer to FIG. 6), and the well W is capable of containing one fertile ovum F.

The well W is provided in the culture dish 2023a, and a culture solution C and oil O are injected into the culture dish 2023a. The oil O has a function of suppressing the evaporation of the culture solution C by coating the culture solution C.

Figure 5:
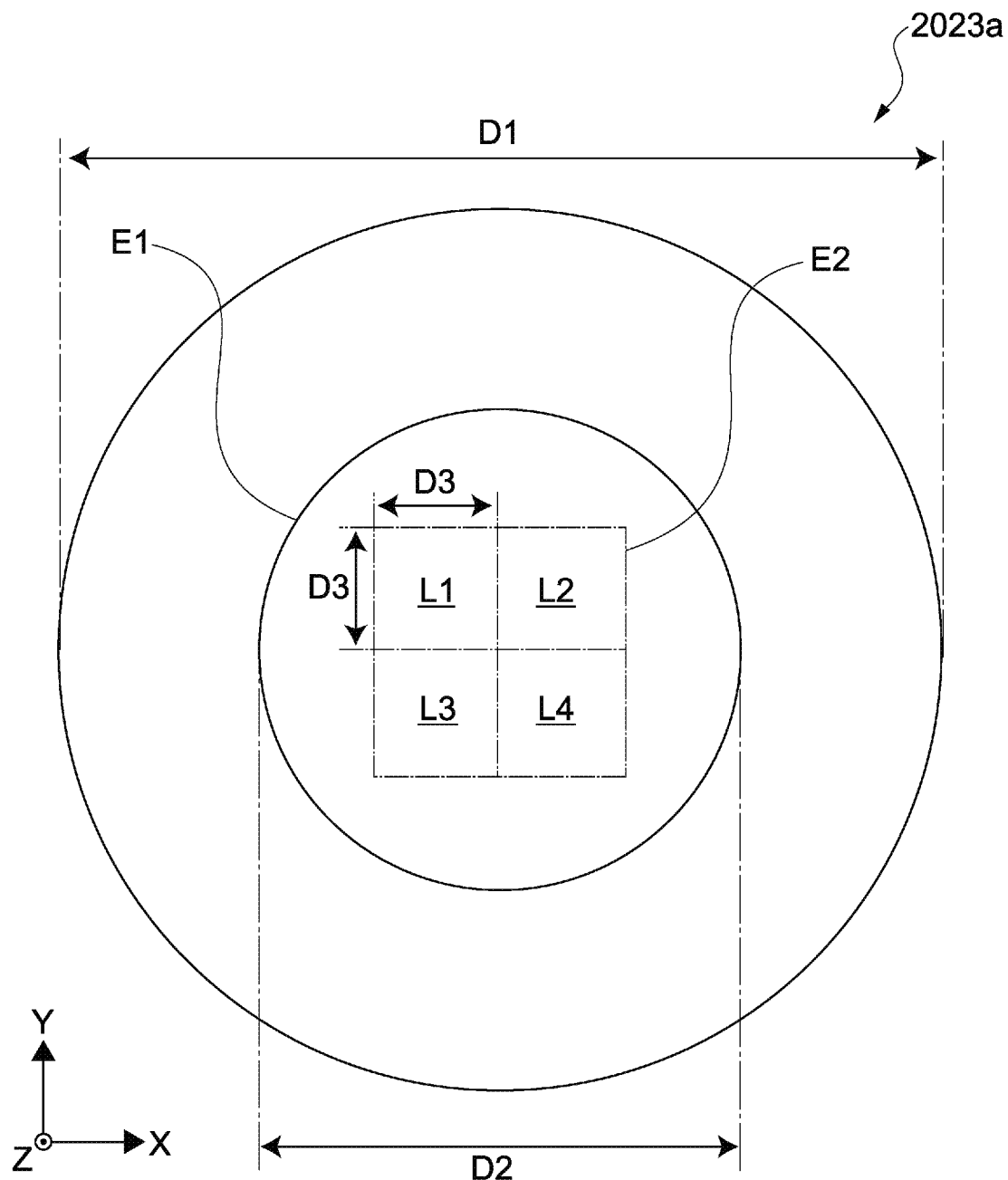
FIG. 5 is a plan view of the culture dish seen from the light source side.

FIG. 5 is a schematic view (a plan view) of the culture dish 2023a seen from the light source 2022 side. The culture dish 2023a includes a well region E1 in which the plurality of wells W are formed. A diameter D1 of the culture dish 23a and a diameter D2 of the well region E1 are not particularly limited, and for example, the diameter D1 is approximately 35 mm, and the diameter D2 is approximately 20 mm.

The well region E1 includes an imaging region E2 which becomes an imaging target of the capturing unit 2021. As illustrated in FIG. 2, the imaging region E2 is equally divided into four imaging areas L1 to L4. A length D3 of one side of each of the imaging areas L1 to L4, for example, is approximately 5 mm.

Figure 6:
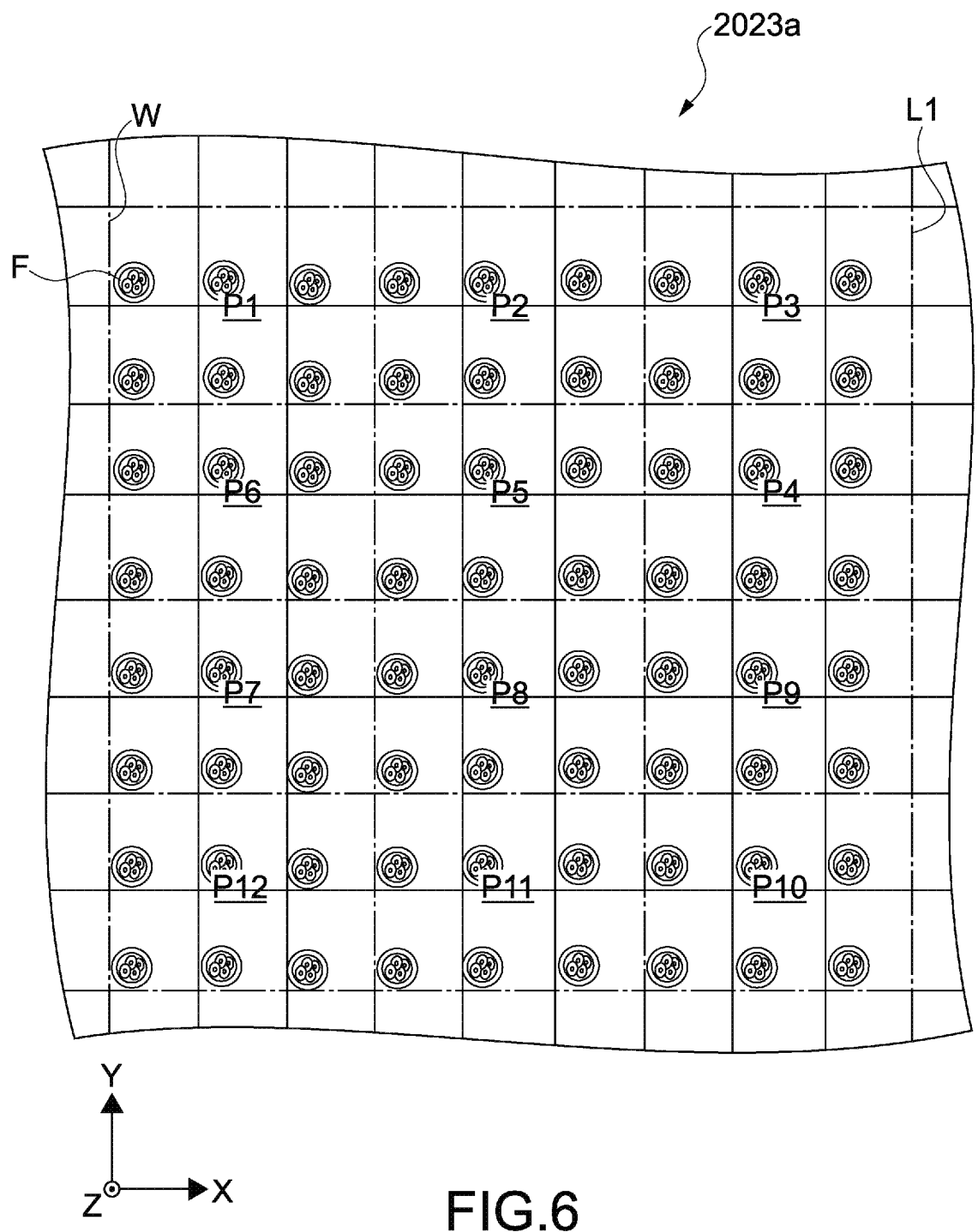
FIG. 6 is a schematic view enlargedly illustrating an imaging area of the culture dish seen from the light source side.

FIG. 6 is a schematic view enlargedly illustrating the imaging area L1 seen from the light source 2022 side. The imaging area L1 includes 72 wells W in the plurality of wells W provided in the well region E1, and is equally divided into twelve position (POS) regions.

Each of the POS regions P1 to P12 includes three wells W in the X axis direction, and six wells W in two rows in the Y axis direction. The capturing unit 2021 according to this embodiment captures the fertile ova F contained in the well W of each of the POS region in chronological order, in a step of "Observation Image?Identification Information Acquisition" described below (refer to FIG. 9). Note that FIG. 6 is a schematic view enlargedly illustrating the imaging area L1, and the imaging areas L2 to L4 also have the same configuration as that of the imaging area L1.

A material configuring the culture dish 2023a is not particularly limited, and for example, is an inorganic material such as glass or silicon, an organic material such as a polystyrene resin, a polyethylene resin, a polypropylene resin, an ABS resin, nylon, an acrylic resin, a fluorine resin, a polycarbonate resin, a polyurethane resin, a methyl pentene resin, a phenolic resin, a melamine resin, an epoxy resin, or a vinyl chloride resin, and the like, and the culture dish 2023a is a transparent body transmitting the light emitted from the light source 2022. Alternatively, a portion of the culture dish 23a other than the portion transmitting the light emitted from the light source 2022 may be formed of the materials described above, and the culture dish 23a may be formed of a metal material.

The humidity?temperature?gas control unit 203 controls the temperature and the humidity in the incubator 201, and the gas introduced into the incubator 201, and establish an environment suitable for growing the fertile ovum F. The humidity?temperature?gas control unit 203 is capable of controlling the temperature in the incubator 201 such that the temperature, for example, is approximately 38?C.

The detection unit 204 is connected to the control recording PC 205 in a wireless manner or a wired manner, detects the temperature in the incubator 201, the atmospheric pressure, an illuminance of the light source 2022, and an oxygen concentration, and the like, and outputs a detection result to the control recording PC 205. The detection unit 204, for example, is a solar panel type or battery type internet of things (IoT) sensor, or the like, and the type thereof is not limited.

The control recording PC 205 is connected to the capturing unit 2021, the light source 2022, the humidity?temperature?gas control unit 203, the detection unit 204, and a gateway terminal 10a. The control recording PC 205 is capable of controlling a culture environment of the fertile ovum F by controlling the capturing unit 2021, the light source 2022, the detection unit 204, and the humidity?temperature?gas control unit 203 on the basis of the output thereof.

The control recording PC 205, for example, is capable of storing culture environment information output from the detection unit 204, and of transmitting the culture environment information to the gateway terminal 10a. Here, the culture environment information of this embodiment, for example, is information relevant to pH of the culture solution C, or the temperature, the humidity, and the oxygen concentration in the incubator 201, and the same applies to the following description.

The gateway terminal 10a receiving the culture environment information transmits information relevant to at least one of pH of the culture solution C, and the temperature, the humidity, and the oxygen concentration in the incubator 201, as the culture environment information, to an acquisition unit 24 (refer to FIG. 7) through the network N. The acquisition unit 24 outputs the acquired culture environment information to the storage unit 28 (refer to FIG. 7), and thus, the culture environment information is stored in the storage unit 28.

In addition, the control recording PC 205 stores information relevant to a sperm and an ovum which become the fertile ovum F, mating information relevant to the fertile ovum F, information relevant to the culture dish 2023a, and the like, as identification information of identifying each of the fertile ova F contained in each of the plurality of wells W. The control recording PC 205 is capable of transmitting the identification information to the gateway terminal 10a. The identification information will be described below.

The display device 206 is capable of displaying an observation image imaged by the capturing unit 2021, the culture environment information, the identification information, and the like. The display device 206, for example, is a display device using a liquid crystal, an organic electroluminescence (EL), and the like.

The input unit 207 is a manipulation device for inputting a manipulation of the fertile ovum manager, such as a keyboard or a mouse. The input unit 207 according to this embodiment may be a touch panel or the like, which is integrated with display device 206.

As illustrated in FIG. 1, it is desirable that the terminal device 10 of this embodiment is configured of the plurality of gateway terminals 10a from the viewpoint of improving an analysis accuracy of the information processing apparatus 50, and may be configured of a single gateway terminal 10a. In this case, the single gateway terminal 10a may be connected to the plurality of observation devices 202 (the fertile ovum manager) in a wireless manner or a wired manner, through the control recording PC 205.

In addition, typically, the gateway terminal 10a is a general-purpose gateway which is capable of mutually converting different protocols or address architectures, but is not limited thereto, and may be a personal computer (PC) or the like, which is set to function as a gateway.

(Information Processing Apparatus)

The information processing apparatus 20 includes hardware which is necessary for a computer, such as a central processing unit (CPU) 21, a read only memory (ROM) 22, and a random access memory (RAM) 23.

The CPU 21 executes a program according to the present technology, which is stored in the ROM 22, by loading the program onto the RAM 23. Accordingly, each block operation of the information processing apparatus 20 described below is controlled.

The ROM 22 is a memory device in which various data items, programs, or the like, used in the information processing apparatus 20, are fixedly stored.

The RAM 23 is a memory element which is used as an operation region for the CPU 21, a temporary storage space of history data, and the like, such as static random access memory (SRAM).

The program, for example, is installed in the information processing apparatus 20 through various storage media (an internal memory). Alternatively, the installation of the program may be executed through the internet or the like. The information processing apparatus 20 of this embodiment is a web server for performing quality evaluation of the fertile ovum F according to cloud computing, but is not limited thereto, and for example, other arbitrary computers such as a PC may be used.

Figure 7:
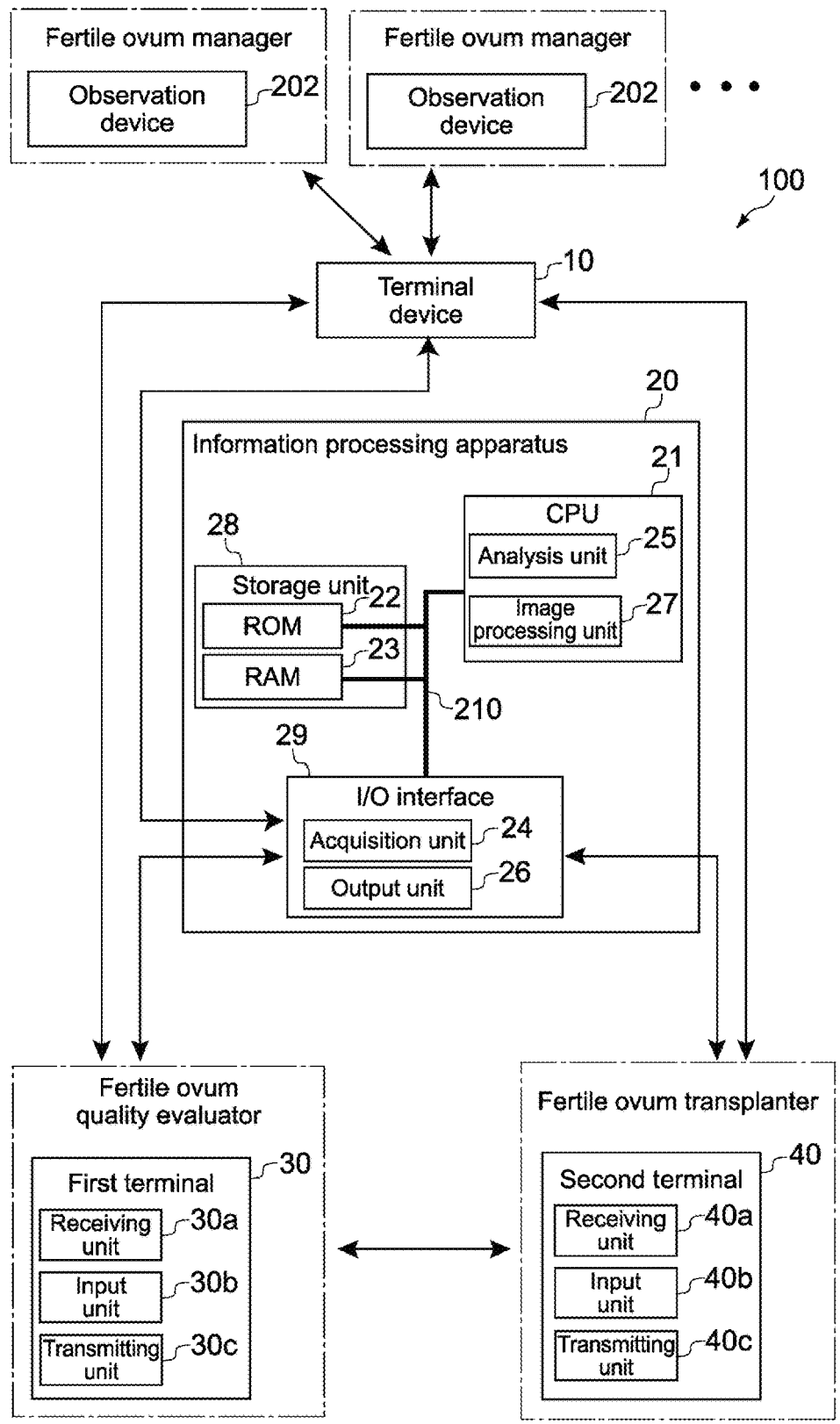
FIG. 7 is a block diagram of a fertile ovum quality evaluation system according to a first embodiment of the present technology.

FIG. 7 is a block diagram of the fertile ovum quality evaluation system 100 according to this embodiment. As illustrated in FIG. 7, the information processing apparatus 20 includes the acquisition unit 24, an analysis unit 25, an output unit 26, an image processing unit 27, a storage unit 28, an I/O interface 29, and a bus 210.

The acquisition unit 24 acquires a plurality of observation images in which the fertile ova F associated with the intrinsic identification information are captured in chronological order, to the plurality of gateway terminals 10a (the terminal device 10) through the network N.

The analysis unit 25 generates fertile ovum analysis information, on the basis of the plurality of observation images in which the fertile ova F are captured in chronological order. The analysis unit 25 of this embodiment includes an identifier which is generated on the basis of an algorithm of setting time-lapse images of fertile ova collected from a plurality of fertile ova managers, to learning data. The identifier will be described below.

The output unit 26 outputs evaluation support information including identification information intrinsic to the fertile ovum F and the fertile ovum analysis information, to a computer receiving the input of the fertile ovum evaluation information based on the evaluation support information, through the network N.

The image processing unit 27 performs predetermined image processing with respect to the plurality of observation images in which the fertile ova F are captured in chronological order. For example, in a case of capturing the fertile ovum F while culturing the fertile ovum F in each of the wells in the culture dish 2023a, the image processing unit 27 performs image segmentation processing (trimming processing) or the like with respect to the plurality of observation images before image analysis (refer to Step S02). Accordingly, it is possible to use an enlarged image in which the fertile ovum F is cut one by one in analysis, and thus, an analysis accuracy is improved.

The storage unit 28, for example, includes the ROM 22 in which the program executed by the CPU 21 is stored, and the RAM 23 which is used as a work memory or the like when CPU 21 execute processing. Further, the storage unit 28 may include a non-volatile memory such as a hard disc drive (HDD) and a flash memory (a solid state drive: SSD). Accordingly, input information input from the terminal device 10, the first terminal 30, and the second terminal 40, an analysis result of the analysis unit 25, and the like can be stored in the storage unit 28.

The I/O interface 29 is connected to the terminal device 10, the first and second terminals 30 and 40 through the network N, such that communication can be performed, and includes the acquisition unit 24 and the output unit 26. The I/O interface 29 functions as an input/output interface between the terminal device 10 and the first and second terminals 30 and 40.

The bus 210 is a signal transmission path for inputting and outputting various signals in each of the units of the information processing apparatus 20. The CPU 21, the ROM 22, the RAM 23, and the I/O interface 29 are connected to each other through the bus 210.

Note that the functions of the acquisition unit 24, the analysis unit 25, the output unit 26, the image processing unit 27, and the storage unit 28 of the information processing apparatus 50 are not limited to the above description, and the detailed functions will be described in the following description of a fertile ovum quality evaluation method.

(First Terminal)

The first terminal 30 is handled by the fertile ovum quality evaluator. The first terminal 30 includes a receiving unit 30a receiving information output from the output unit 26 or the second terminal 40, an input unit 30b receiving the input from the fertile ovum quality evaluator, and a transmitting unit 30c transmitting the information input through the input unit 30b or the information received by the receiving unit 30a, through the network N.

Typically, the first terminal 30 is a computer such as a laptop PC or a desktop PC, but is not limited thereto, and for example, may be a smart device, a tablet terminal, or the like.

(Second Terminal)

The second terminal 40 is handled by the fertile ovum transplanter. The second terminal 40 includes a receiving unit 40a receiving information output from the output unit 26 or the first terminal 30, an input unit 40b receiving the input from the fertile ovum transplanter, and a transmitting unit 40c transmitting the information input through the input unit 40b, the information received by the receiving unit 40a, through the network N.

Typically, the second terminal 40 is a smart device, a tablet terminal, or the like, but is not limited thereto, and for example, may be other arbitrary computers such as a laptop PC or a desktop PC.

<Fertile Ovum Quality Evaluation Method>

Figure 8:
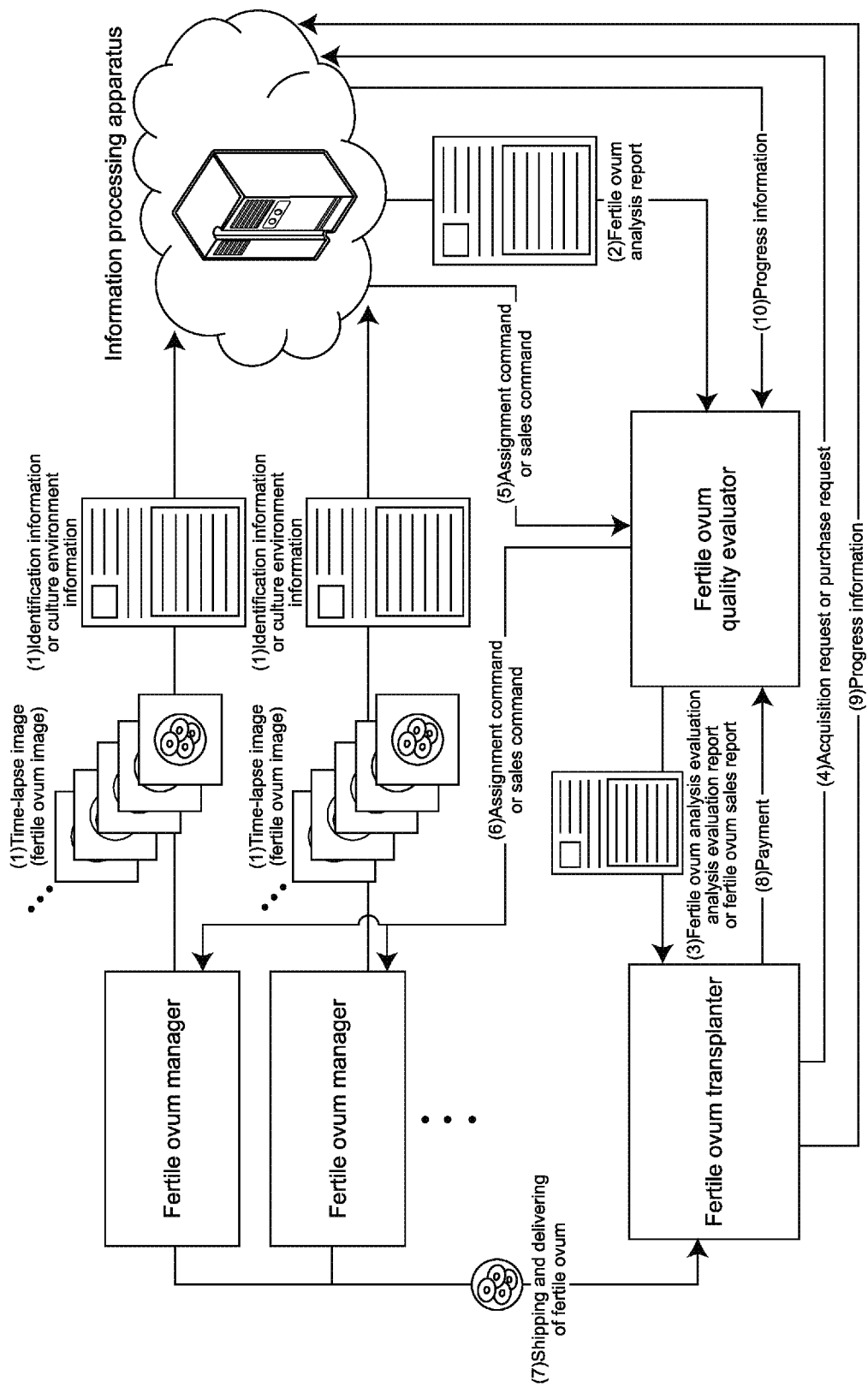
FIG. 8 is a diagram illustrating a business model of the fertile ovum quality evaluation system.
Figure 9:
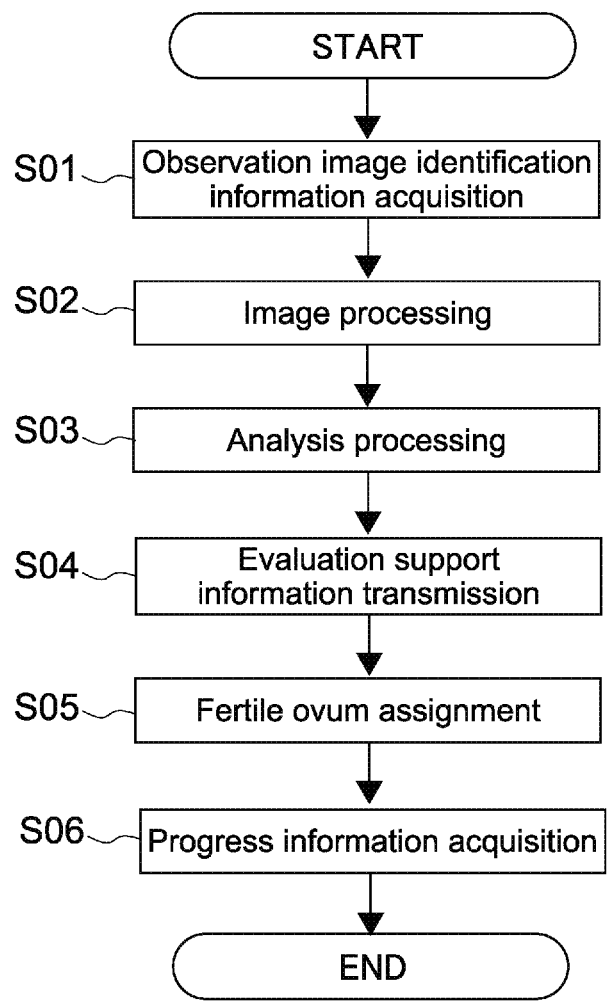
FIG. 9 is a flowchart illustrating a method of evaluating quality of a fertile ovum of the fertile ovum quality evaluation system.

FIG. 8 is a diagram illustrating a business model of the fertile ovum quality evaluation system 100 according to this embodiment, and is a diagram illustrating a flow of analyzing the quality of the fertile ovum F and of obtaining progress information relevant to the fertile ovum F. FIG. 9 is a flowchart illustrating a method of evaluating the quality of the fertile ovum F of the fertile ovum quality evaluation system 100. Hereinafter, a quality evaluation method of the fertile ovum F will be described, while suitably referring to FIG. 9.

(Step S01: Observation Image?Identification Information Acquisition)

First, the fertile ovum quality evaluator inputs the identification information relevant to the fertile ovum F into control recording PC 205 through the input unit 207. The identification information input into the control recording PC 205 is stored in the control recording PC 205, and is transmitted to the gateway terminal 10a. The gateway terminal 10a receiving the identification information transmits the identification information to the acquisition unit 24 through the network N, and the acquisition unit 24 acquires the identification information.

Here, the identification information of this embodiment, for example, is the information relevant to the sperm and the ovum which become the fertile ovum F, the mating information relevant to the fertile ovum F, and the information relevant to the culture dish 2023a, and the same applies to the following description. The acquisition unit 24 acquires at least one of the information items, as the identification information.

In a case of describing the sperm, the information relevant to the sperm and the ovum which become the fertile ovum F, for example, is the amount of seminal fluid, the total number of sperms, the total number of motile sperms, viscosity, a sperm concentration, a forward movement rate, a non-forward movement rate, a normal morphological rate, a motile sperm concentration (MSC), a high-speed forward movement sperm concentration (PMSC-a), a low-speed forward movement sperm concentration (PMSC-b), a functional motile sperm concentration (FSC), a sperm motility index (SMI), an average sperm speed, and the like.

On the other hand, in a case of describing the ovum, the information relevant to the sperm and the ovum which become the fertile ovum F, for example, is the amount of ova, the total number of ova, ovum age, an anti-Mullerian duct hormone (AMH) value, a luteotrophic hormone (LH) value, a follicle stimulation hormone (FSH) value, an estradiol (E2) value, a progesterone (P4) value, an estrogenic hormone (estrogen) value, and the like.

The mating information relevant to the fertile ovum F, for example, information relevant to a male from whom the sperm is sampled (a weight, a height (a body height), an age, a blood, medical history, a health condition, and the like), information relevant to a female from whom the ovum is sampled (a weight, a height (a body height), an age, a blood, medical history, an ovary age, the total number of times of parturition, a health condition, a parturition record, and the like), or the like.

The information relevant to the culture dish 2023a, for example, is information relevant to the position of the culture dish 2023a such as in which culture dish 2023a of six culture dishes 2023a on the observation stage S, the fertile ovum F which becomes an evaluation target, is contained (refer to FIG. 3), information relevant to the position of the fertile ovum F such as in which area of four imaging areas L1 to L4, the fertile ovum F which becomes the evaluation target, exists (refer to FIG. 5), or the like.

Subsequently, the output unit 26 receives the fact that the acquisition unit 24 acquires the identification information from the gateway terminal 10a through the network N, and outputs a capturing command of capturing the fertile ovum F associated with the identification information to the gateway terminal 10a through the network N. The gateway terminal 10a receiving the capturing command transmits the capturing command to the control recording PC 205.

Figure 10:
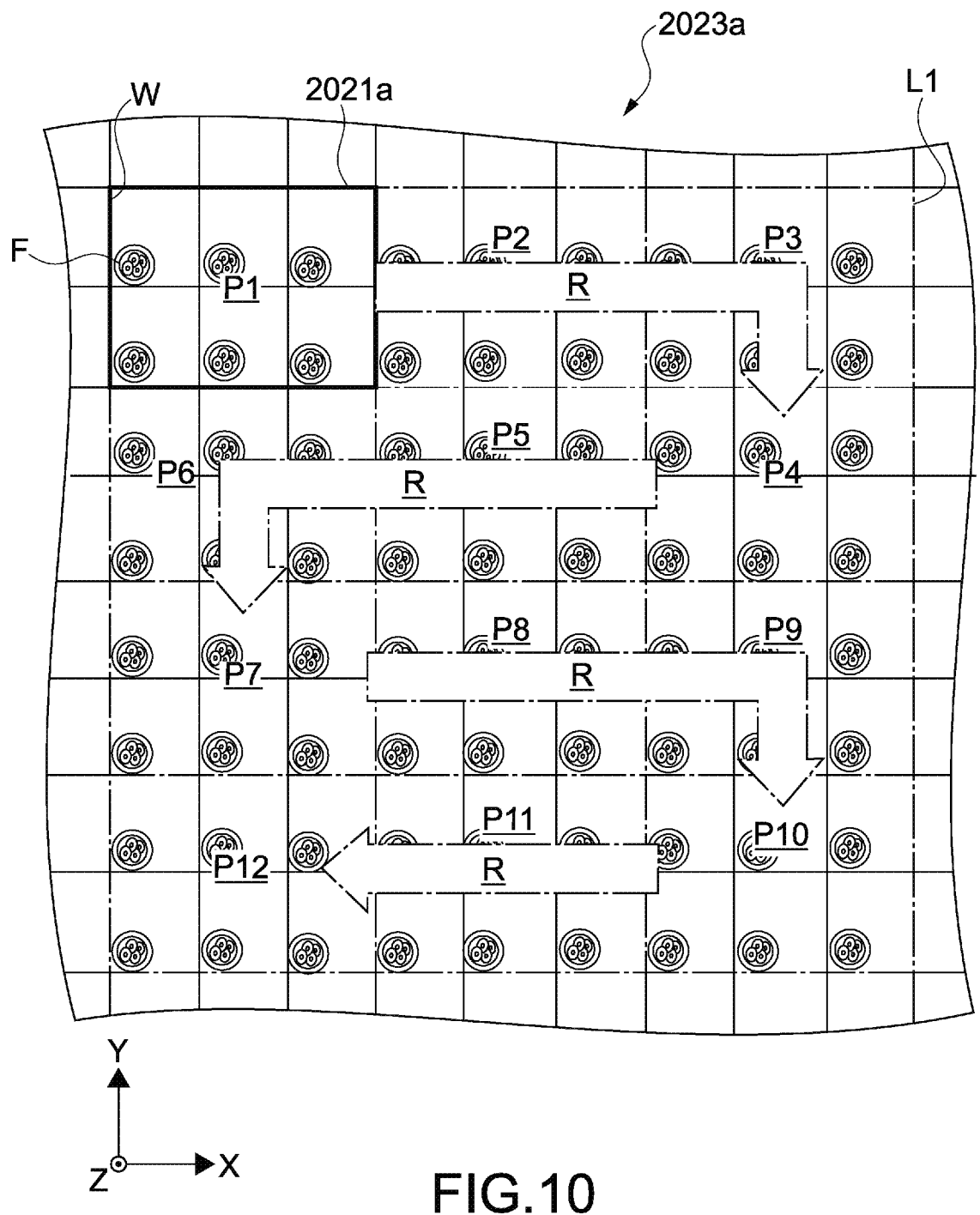
FIG. 10 is a schematic view illustrating a state in which a capturing unit of the present technology captures a plurality of fertile ova.

FIG. 10 is a schematic view illustrating a state in which the capturing unit 2021 captures the plurality of fertile ova F, and is a diagram illustrating a movement route of the capturing unit 2021. The control recording PC 205 receiving the capturing command controls the capturing unit 2021, according to the capturing command.

Accordingly, the plurality of fertile ova F respectively contained in the plurality of wells W are captured in chronological order, in each of the position (POS) regions. At this time, as illustrated in FIG. 10, a visual field range 2021a of the capturing unit 2021 is moved in the order from the POS region P1 to the POS region P12 at intervals of approximately three seconds, according to a movement route R.

Then, such an operation is performed with respect to all of the culture dishes 2023a mounted on the observation stage S, and is repeated specified number of times. Accordingly, an image including six fertile ova F (hereinafter, a first time-lapse image G1) is generated, and the first time-lapse image G1 is transmitted to the control recording PC 205.

The control recording PC 205 into which the first time-lapse image G1 is input, transmits the first time-lapse image G1 to the gateway terminal 10a. The gateway terminal 10a receiving the first time-lapse image G1 transmits the first time-lapse image G1 to the acquisition unit 24 through the network N, and the acquisition unit 24 acquires the first time-lapse image G1.

Figure 11:
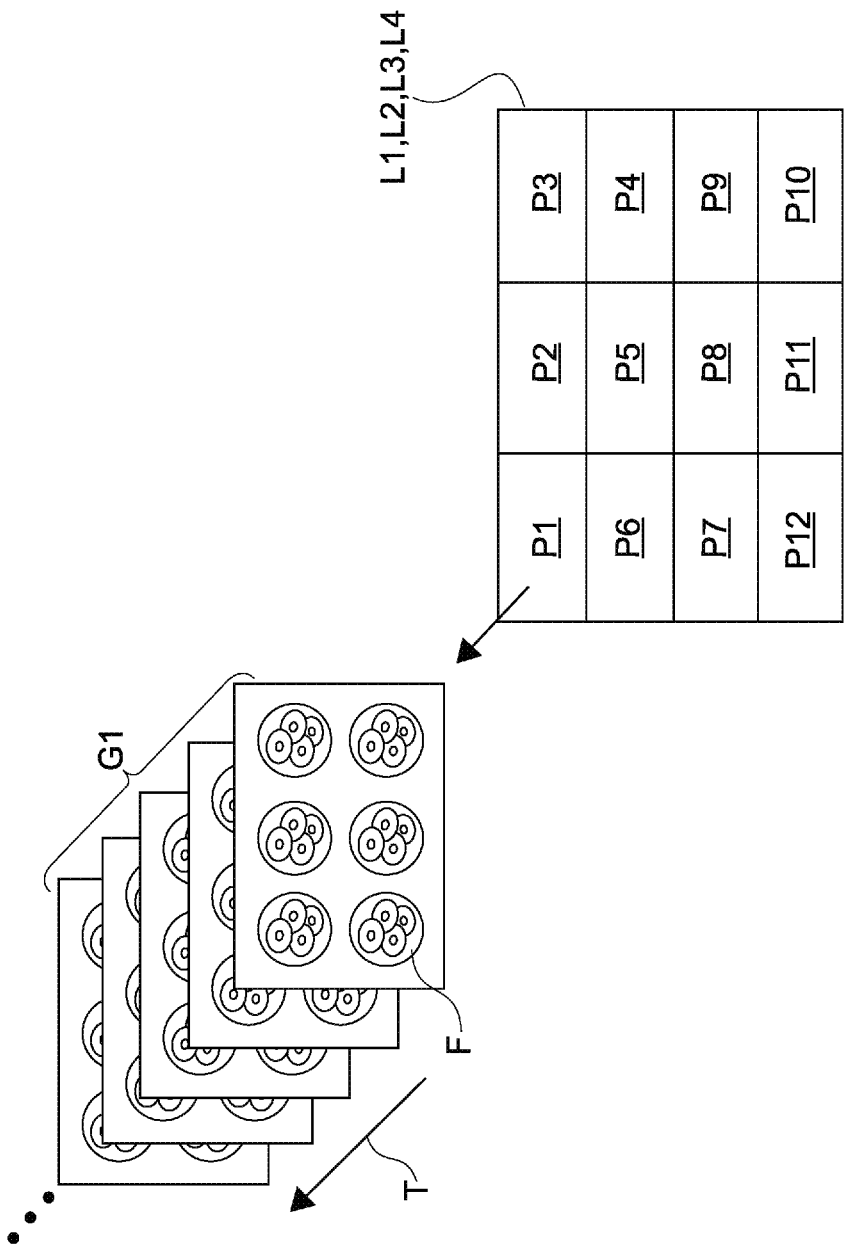
FIG. 11 is a conceptual diagram virtually illustrating a first time-lapse image.

FIG. 11 is a conceptual diagram virtually illustrating the first time-lapse image G1. As illustrated in FIG. 11, the first time-lapse images G1 of this embodiment are respectively generated with respect to the POS regions P1 to P12, in chronological order, along a time axis T. Herein, a plurality of observation image data items in chronological order, illustrated in FIG. 11, are referred to as the first time-lapse image G1.

A capturing interval or the number of captured images of the capturing unit 2021 in the observation system 200 can be arbitrarily set. For example, in a case where a capturing period is one week, the capturing interval is 15 minutes, and nine stacks of images are captured by changing a focal point distance in a depth direction (the Z axis direction), approximately 6000 laminated images including six fertile ova F can be obtained with respect to one POS region. Accordingly, a three-dimensional image of the fertile ovum F can be acquired.

The acquisition unit 24 outputs the first time-lapse image G1 and the identification information which are acquired from the gateway terminal 10a, to the storage unit 28 through the network N, and the storage unit 28 stores the first time-lapse image G1 and the identification information. In addition, the acquisition unit 24 outputs the acquired first time-lapse image G1 to the image processing unit 27, and outputs the identification information to the output unit 26.

(Step S02: Image Processing)

The image processing unit 27 performs processing (trimming) with respect to the first time-lapse image G1 output from the acquisition unit 24, in the fertile ovum F unit. Accordingly, an image including one fertile ovum F (Hereinafter, a second time-lapse image G2) is generated. Next, the image processing unit 27 outputs the second time-lapse image G2 to the storage unit 28, and the second time-lapse image G2 is stored in the storage unit 28.

Figure 12:
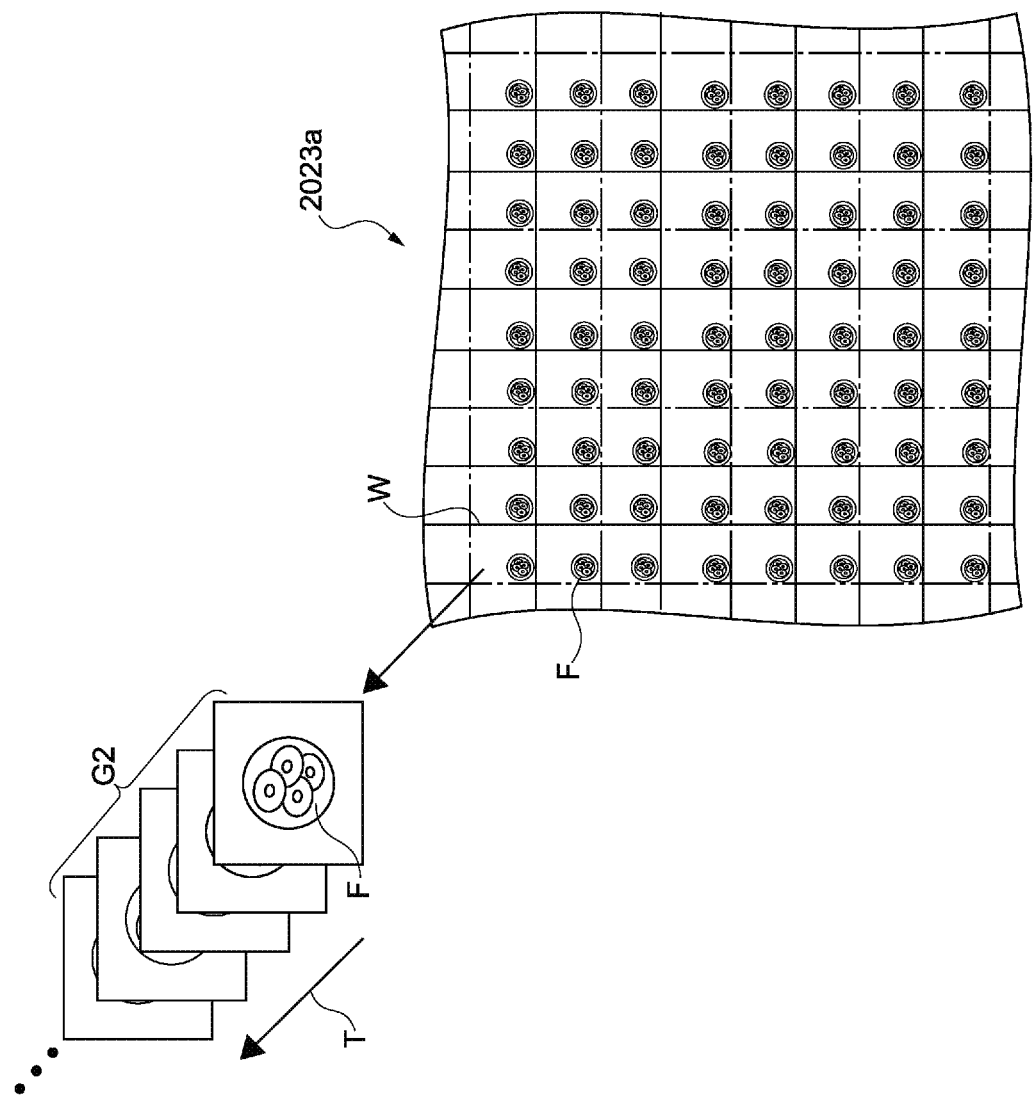
FIG. 12 is a conceptual diagram virtually illustrating a second time-lapse image.

FIG. 12 is a conceptual diagram virtually illustrating the second time-lapse image G2. As illustrated in FIG. 12, the second time-lapse images G2 of this embodiment are respectively generated with respect to the plurality of wells W, in chronological order, along the time axis T. Herein, a plurality of observation image data items in chronological order, illustrated in FIG. 12, are referred to as the second time-lapse image G2.

Next, the image processing unit 27 performs predetermined image processing with respect to the second time-lapse image G2. The second time-lapse image G2 subjected to the image processing by the image processing unit 27, is output to the analysis unit 25 and the storage unit 28, and the second time-lapse image G2 is stored in the storage unit 28. Hereinafter, several application examples of Step S02 will be described.

Application Example 1

The image processing unit 27 executes normalization with respect to each image configuring the second time-lapse image G2. Accordingly, for example, it is possible to not only remove a noise in the second time-lapse image G2, but also uniformize the second time-lapse image before the analysis. Accordingly, the characteristics of the second time-lapse image are easily extracted.

The normalization which is performed with respect to the second time-lapse image G2 by the image processing unit 27 of this embodiment, for example, is normalization processing of unifying shades, brightnesses, or the like of each of the images configuring the second time-lapse image G2, or standardization processing, non-correlation processing, whitening processing, or the like.

Application Example 2

The image processing unit 27 performs probability processing, binarization processing, overlay processing, and the like according to deep learning analysis, with respect to the second time-lapse image G2. Accordingly, for example, a profile line of the fertile ovum F in the second time-lapse image G2 is extracted.

Application Example 3

The image processing unit 27 forms a mask region along the shape of the fertile ovum F, instead of each of the images configuring the second time-lapse image G2. Accordingly, an analysis region (a recognition region) of the fertile ovum F in the second time-lapse image G2 becomes clear, and thus, the shape of the fertile ovum F can be accurately recognized. According to such a technology, for example, a transparent layer forming the outer shape of the fertile ovum F, or the shape of a blastodermic vesicle, a cell blastomere, a morula, and the like in the fertile ovum F can be accurately recognized.

(Step S03: Analysis Processing)

Figure 13:
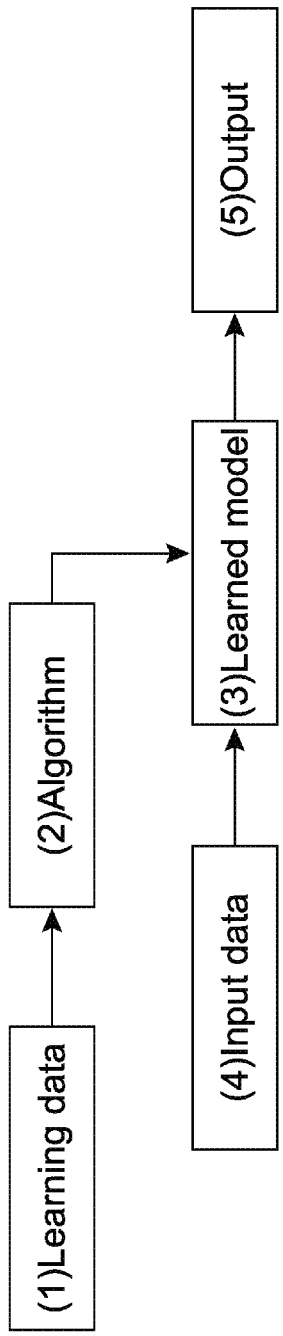
FIG. 13 is a block diagram illustrating a processing procedure of general specialized AI in a simplified manner.

The information processing apparatus 20 of this embodiment is a cloud server using so-called specialized artificial intelligence (AI), which replaces an intellectual operation of a user. FIG. 13 is a block diagram illustrating a processing procedure of general specialized AI in a simplified manner.

The specialized AI is a mechanism in which arbitrary input data is applied to a learned model built out by installing learning data in an algorithm functioning as a learning program, and thus, an output can be obtained, as a large frame. For example, the learned model may be a trained statistical model such as a classifier, neural network or other suitable type of statistical model trained using the learning data. Hereinafter, several application examples of Step S03 will be described while suitably referring to FIG. 13.

Application Example 1

The analysis unit 25 reads out at least one of shape information, motion information, compaction information, contraction information, expansion information, dormant information, growing information according to findings, and quality information, based on the time-lapse images of the fertile ova collected from the plurality of fertile ova managers through the network N, which are stored in advance in the storage unit 28, from the storage unit 28. Such information corresponds to "Learning Data" of FIG. 13.

Here, the quality information, for example, is information relevant to a growing condition or a quality ranking of the fertile ovum F, or the transparent layer of the fertile ovum F, the cell in the fertile ovum F (the blastodermic vesicle, the cell blastomere, the morula, and the like), a pronucleus, a polocyte, a nucleus in the blastomere, fragmentation, an egg cell marginal transparent region (Halo), and the like.

The shape information, for example, is information relevant to a change in the diameter, the area, the volume, the roundness, and the like of the fertile ovum F in chronological order, while the fertile ovum F is grown.

The motion information, for example, is information relevant to a change in a motion amount of the cell in the fertile ovum F in chronological order, while the fertile ovum F is grown. The change in the motion amount, for example, is a change in the minimum speed, the maximum speed, the maximum speed of acceleration, the average speed, the average speed of acceleration, the central value, and the standard deviation of a motion vector of the cell in the fertile ovum F, or the total value of a motion speed vector of the cell in the fertile ovum F, the total value of a vector of a motion speed of acceleration of the cell in the fertile ovum F, or the like, in chronological order.

The compaction information, for example, is a compaction (a condition in which the divided cells are fused, and become one mass) time or the like when the shape of the fertile ovum F is changed from a 16-cell stage to a morula stage.

The contraction information, for example, the number of times of contraction, a contraction diameter, a contraction speed, a contraction time, a contraction interval, a contraction strength, a contraction frequency, and the like of the fertile ovum F, while the fertile ovum F is grown. The expansion information, for example, is the number of times of expansion, an expansion diameter, an expansion speed, an expansion time, an expansion interval, an expansion strength, an expansion frequency, and the like of the fertile ovum F, while the fertile ovum F is grown.

The dormant information, for example, is information relevant to a lag-phase (a cell telogen), while the fertile ovum F is grown.

The growing information according to findings, for example, information relevant to the quality of the fertile ovum (a growing condition, the number of cells, cell symmetry, the number of pronuclei, the number of polocytes, the number of nuclei in the cell blastomere, a fragment, or the like), which is determined by an expert such as the embryologist, according to the findings, on the basis of the time-lapse images of the fertile ova captured in chronological order.

Note that "Shape Information", "Motion Information", "Compaction Information", "Contraction Information", "Expansion Information", "Dormant Information", "Growing Information according to Findings", and "Quality Information", described above, are the same in the following description.

Next, the analysis unit 25 builds out a first identifier by installing the learning data read out from the storage unit 28 in a first algorithm set in advance. Accordingly, the analysis unit 25 includes the first identifier.

Note that the first algorithm corresponds to "Algorithm" of FIG. 13, and for example, functions as a machine learning algorithm. In addition, the first identifier corresponds to "Learned Model" of FIG. 13. Typically, the first identifier of this embodiment is configured of a single learned model, but is not limited thereto, and for example, may have a configuration in which a plurality of learned models are combined.

The type of machine learning algorithm is not particularly limited, and for example, may be an algorithm using a neural network such as a recurrent neural network (RNN), a convolutional neural network (CNN), or a multilayer perceptron (MLP), or may be an arbitrary algorithm of executing a supervised learning method, an unsupervised learning method, a semi-supervised learning method, a reinforcement learning method, and the like.

Next, the analysis unit 25 generates first fertile ovum analysis information by applying the first identifier built out as described above, to the second time-lapse image G2 output from the image processing unit 27.

Specifically, the second time-lapse image is subjected to the deep learning analysis by the first identifier, and thus, the first fertile ovum analysis information is generated. Then, the analysis unit 25 outputs the first fertile ovum analysis information to the output unit 26 and the storage unit 28, and the first fertile ovum analysis information is stored in the storage unit 28.

Here, the analysis unit 25 of this embodiment generates at least one of a capturing time during which the capturing unit 2021 captures the fertile ovum F, a growing time (a culturing time) of the fertile ovum F, the quality information, the shape information, the motion information, the compaction information, the contraction information, the expansion information, and the dormant information, as the first fertile ovum analysis information.

Note that in Step S03, the second time-lapse image G2 corresponds to "Input Data" of FIG. 13, and the first fertile ovum analysis information corresponds to "Output" of FIG. 13.

Application Example 2

The analysis unit 25 reads out at least one of the shape information, the motion information, the compaction information, the contraction information, the expansion information, the dormant information, the growing information according to findings, and the quality information, based on the identification information of the fertile ova collected from the plurality of fertile ova managers through the network N, and the time-lapse images of the fertile ova, which are stored in advance in the storage unit 28, from the storage unit 28. Such information corresponds to "Learning Data" of FIG. 13.

Next, the analysis unit 25 builds out an identifier by installing the learning data read out from the storage unit 28 in an algorithm set in advance. Accordingly, the analysis unit 25 includes the identifier.

Note that the algorithm corresponds to "Algorithm" of FIG. 13, and for example, functions as the machine learning algorithm described above. In addition, the identifier corresponds to "Learned Model" of FIG. 13.

Next, the analysis unit 25 generates the first fertile ovum analysis information by applying the identifier built out as described above, to the second time-lapse image G2 output from the image processing unit 27, and the identification information of the fertile ovum F associated with the second time-lapse image G2.

Specifically, the second time-lapse image and the identification information intrinsic to the fertile ovum F are subjected to the deep learning analysis by the identifier, and thus, the first fertile ovum analysis information is generated. Then, the analysis unit 25 outputs the first fertile ovum analysis information to the output unit 26 and the storage unit 28, and the first fertile ovum analysis information is stored in the storage unit 28.

Note that the second time-lapse image G2, and the identification information relevant to the fertile ovum F associated with the image G2, correspond to "Input Data" of FIG. 13, and the first fertile ovum analysis information corresponds to "Output" of FIG. 13.

Application Example 3

The analysis unit 25 reads out at least one of the shape information, the motion information, the compaction information, the contraction information, the expansion information, the dormant information, the growing information according to findings, and the quality information, based on the culture environment information of the fertile ova collected from the plurality of fertile ova managers through the network N, and the time-lapse images of the fertile ova, which are stored in advance in the storage unit 28, from the storage unit 28. Such information corresponds to "Learning Data" of FIG. 13.

Next, the analysis unit 25 builds out an identifier by installing the learning data read out from the storage unit 28 in an algorithm set in advance. Accordingly, the analysis unit 25 includes the identifier.

Note that the algorithm corresponds to "Algorithm" of FIG. 13, and for example, functions as the machine learning algorithm described above. In addition, the identifier corresponds to "Learned Model" of FIG. 13.

Next, the analysis unit 25 generates the first fertile ovum analysis information by applying the identifier built out as described above, to the second time-lapse G2 output from the image processing unit 27, and the culture environment information of the fertile ovum F associated with the second time-lapse image G2.

Specifically, the second time-lapse image G2 and the culture environment information are subjected to the deep learning analysis by the identifier, and thus, the first fertile ovum analysis information is generated. Then, the analysis unit 25 outputs the first fertile ovum analysis information to the output unit 26 and the storage unit 28, and the first fertile ovum analysis information is stored in the storage unit 28.

Note that the second time-lapse image G2, and the culture environment information relevant to the fertile ovum F associated with the time-lapse image G2 correspond to "Input Data" of FIG. 13, and the first fertile ovum analysis information corresponds to "Output" of FIG. 13.

Application Example 4

The analysis unit 25 reads out at least one of the shape information, the motion information, the compaction information, the contraction information, the expansion information, the dormant information, the growing information according to findings, and the quality information, based on the time-lapse images of the fertile ova collected from the plurality of fertile ova managers through the network N, which are stored in advance in the storage unit 28, from the storage unit 28. Such information corresponds to "Learning Data" of FIG. 13.

Next, the analysis unit 25 builds out a second identifier by installing the learning data read out from the storage unit 28 in the first algorithm and the second algorithm set in advance. Accordingly, the analysis unit 25 includes the second identifier.

Note that the first algorithm and the second algorithm correspond to "Algorithm" of FIG. 13, and for example, function as the machine learning algorithm as described above. In addition, the second identifier corresponds to "Learned Model" of FIG. 13. In this embodiment, two algorithms are used in order to build out the second identifier, but the second identifier is not limited thereto. For example, a plurality of algorithms different from the first algorithm, may be used in order to build out the second identifier.

Next, the analysis unit 25 generates the first fertile ovum analysis information by applying the second identifier built out as described above, to the second time-lapse image G2 output from the image processing unit 27. Specifically, the second time-lapse image G2 is subjected to the deep learning analysis by the second identifier, and thus, the first fertile ovum analysis information is generated.

Accordingly, an analysis accuracy of the analysis unit 25 at the time of generating the first fertile ovum analysis information is improved. Then, the analysis unit 25 outputs the first fertile ovum analysis information to the output unit 26 and the storage unit 28, and the first fertile ovum analysis information is stored in the storage unit 28.

Note that the second time-lapse image G2 corresponds to "Input Data" of FIG. 13, and the first fertile ovum analysis information corresponds to "Output" of FIG. 13.

(Step S04: Evaluation Support Information Transmission)

The output unit 26 generates the evaluation support information including at least the identification information acquired from the acquisition unit 24, and the first fertile ovum analysis information acquired from the analysis unit 25. Then, the output unit 26 outputs the evaluation support information to the fertile ovum quality evaluator through the network N.

The evaluation support information, for example, is transmitted to the first terminal 30 as "Fertile Ovum Analysis Report" for a fertile ovum quality evaluator. "Fertile Ovum Analysis Report" may be displayed on the first terminal 30 through application software for a fertile ovum quality evaluator, which is installed in the first terminal 30. At this time, the first terminal 30 displays a fertile ovum analysis report including at least one of the capturing time during which the capturing unit 2021 captures the fertile ovum F, the growing time (the culturing time) of the fertile ovum F, the quality information, the shape information, the motion information, the compaction information, the contraction information, the expansion information, and the dormant information, on a web browser, as the first fertile ovum analysis information.

The first terminal 30 (the receiving unit 30a) receiving the evaluation support information, for example, displays the evaluation support information on the web browser, as a WEB dashboard. Accordingly, the quality evaluation of the fertile ovum F according to the fertile ovum quality evaluator, is supported. Specifically, the fertile ovum evaluation information based on the evaluation support information is input into the first terminal 30 through the input unit 30b, according to the fertile ovum quality evaluator evaluating?browsing the evaluation support information (the fertile ovum analysis report) displayed on the first terminal 30.

At least some of the evaluation support information displayed on the web browser may be modified by the fertile ovum quality evaluator by interacting with the web browser. Here, the fertile ovum evaluation information of this embodiment, for example, is a comment from the fertile ovum quality evaluator evaluating?browsing the evaluation support information, an ID of a straw for cryopreservation cryopreserving the fertile ovum F, a quality evaluation result with respect to the fertile ovum F obtained from the fertile ovum quality evaluator browsing (finding) the evaluation support information, or the like, and the same applies to the following description.

Note that the comment from the fertile ovum quality evaluator, for example, is support information relevant to transplant?fetation?parturition?propagation in order to transplant and propagate the fertile ovum F, support information relevant to fattening?fodder?shipping (selling) in order to raise the immatures generated after the transplant to be sold in the market.

(Step S05: Fertile Ovum Assignment)

In Step S05, the evaluation support information (the first fertile ovum analysis information and the identification information) acquired from the output unit 26, and the fertile ovum evaluation information input by the fertile ovum quality evaluator, are transmitted to the fertile ovum transplanter from the first terminal 30 through the network N. Hereinafter, several application examples of Step S05 will be described.

Application Example 1

The evaluation support information and the fertile ovum evaluation information, transmitted to the second terminal 40, for example, are transmitted to the second terminal 40, as "Fertile Ovum Analysis?Evaluation Report" for a fertile ovum transplanter. "Fertile Ovum Analysis?Evaluation Report", for example, may be displayed on the second terminal 40 through application software for a fertile ovum transplanter installed in the second terminal 40.

The second terminal 40 (the receiving unit 40a) acquiring the evaluation support information (the first fertile ovum analysis information and the identification information) and the fertile ovum evaluation information, for example, displays the information on the web browser, as the WEB dashboard. Accordingly, the fertile ovum transplanter is capable of selecting the fertile ovum F having desired quality, with reference to the fertile ovum analysis?evaluation report (the evaluation support information and the fertile ovum evaluation information), and a selecting operation of the fertile ovum F is supported by the fertile ovum transplanter.

Subsequently, the fertile ovum transplanter inputs an acquisition request of acquiring the fertile ovum F into the second terminal 40 through the input unit 40b, on the basis of the evaluation support information (the first fertile ovum analysis information and the identification information) and the fertile ovum evaluation information, which are displayed on the second terminal 40. The acquisition request, for example, is information of the desired number of acquired fertile ova such as how many fertile ova F the fertile ovum transplanter acquires, information of a shipping and delivery destination of the selected fertile ovum F, and the like, and the same applies to the following description.

The second terminal 40 into which the acquisition request is input from the fertile ovum transplanter, transmits the acquisition request to the acquisition unit 24 through the transmitting unit 40c, through the network N. Next, the output unit 26 receives the fact that the acquisition unit 24 acquires the acquisition request from the second terminal 40 through the network N, and outputs an assignment command according to the acquisition request to the first terminal 30. The assignment command is a command of allowing the fertile ovum transplanter to accelerate the shipping and delivery of the fertile ovum F by taking out the fertile ovum F selected by the fertile ovum transplanter, on the basis of the fertile ovum analysis?evaluation report, from the well W, and the same applies to the following description.

Next, the fertile ovum quality evaluator receives the fact that the first terminal 30 receives the assignment command from the output unit 26, and transmits the assignment command to the gateway terminal 10a through the network N. Then, the gateway terminal 10a receiving the assignment command from the first terminal 30 outputs the assignment command to the control recording PC 205.

The control recording PC 205 into which the assignment command is input, displays the information according to the assignment command, on the display device 206. Accordingly, the assignment command according to the acquisition request of the fertile ovum transplanter, is notified to the fertile ovum manager managing the fertile ovum F. Then, the fertile ovum manager to whom the assignment command is notified, performs the shipping and delivery of the fertile ovum F selected by the fertile ovum transplanter, on the basis of the acquisition request of the fertile ovum transplanter.

Application Example 2

The evaluation support information and the fertile ovum evaluation information, which are transmitted to the second terminal 40, for example, are transmitted to the second terminal 40, as "Fertile Ovum Sales Report" for a fertile ovum transplanter. "Fertile Ovum Sales Report", for example, may be displayed on the second terminal 40 through application software for a fertile ovum transplanter, which is installed in the second terminal 40.

The second terminal 40 (the receiving unit 40a) acquiring the evaluation support information (the first fertile ovum analysis information and the identification information) and the fertile ovum evaluation information, for example, displays the information on the web browser, as the WEB dashboard. The price applied to each of the plurality of fertile ova F is displayed on the WEB dashboard, on the basis of the first fertile ovum analysis information, the identification information, and the fertile ovum evaluation information.

The fertile ovum transplanter inputs the purchase request of purchasing the fertile ovum F into the second terminal 40 through the input unit 40b, on the basis of the evaluation support information (the first fertile ovum analysis information and the identification information) and the fertile ovum evaluation information, which are displayed on the second terminal 40. The purchase request, for example, is information of the desired number of purchased fertile ova such as how many fertile ova F the fertile ovum transplanter purchases, information of the purchased cost according to the desired number of purchased fertile ova, and the like, and the same applies to the following description.

The second terminal 40 into which the purchase request is input from the fertile ovum transplanter, transmits the purchase request to the acquisition unit 24 through the transmitting unit 40c, through the network N. Next, the output unit 26 receives the fact that the acquisition unit 24 acquires the purchase request from the second terminal 40, and transmits a sales command according to the purchase request to the first terminal 30 through the network N. The sales command is a command of allowing the fertile ovum transplanter to accelerate the sales of the fertile ovum F by taking out the fertile ovum F selected by the fertile ovum transplanter, on the basis of the fertile ovum sales report, from the well W.

Next, the fertile ovum quality evaluator receives the fact that the first terminal 30 receives the sales command from the output unit 26, and transmits the sales command to the gateway terminal 10a through the network N. Then, the gateway terminal 10a receiving the sales command from the first terminal 30 outputs the sales command to the control recording PC 205.

The control recording PC 205 into which the sales command is input, displays the information according to the sales command, through the display device 206. Accordingly, the sales command according to the purchase request of the fertile ovum transplanter is notified to the fertile ovum manager managing the fertile ovum F. Then, the fertile ovum manager to which the sales command is notified, performs the shipping and delivery of the fertile ovum F selected by the fertile ovum transplanter, on the basis of the purchase request of the fertile ovum transplanter.

Next, in a case where the fertile ovum transplanter receives the fertile ovum F selected by himself from the fertile ovum manager, the fertile ovum transplanter pays the price based on the purchase request input into the second terminal 40 to the fertile ovum quality evaluator. The payment of the fertile ovum transplanter purchasing the fertile ovum F with respect to the fertile ovum quality evaluator may be performed by mail or through bank transfer, or may be executed by online payment using a dedicated application for a fertile ovum transplanter, which is installed in the second terminal 40.

(Step S06: Progress Information Acquisition)

The fertile ovum transplanter transplants the fertile ovum F which is shipped and delivered from the fertile ovum manager, to the livestock, and performs parturition and propagation. Then, immatures generated from the livestock are grown to the imago, and the imago is sold in the market. The fertile ovum transplanter obtains the progress information relevant to the fertile ovum F selected by himself, on the basis of the evaluation support information (the first fertile ovum analysis information and the identification information) and the fertile ovum evaluation information, while the fertile ovum F assigned from the fertile ovum manager is grown to the imago to be sold.

Next, the fertile ovum transplanter inputs the progress information obtained as described above, into the second terminal 40. Accordingly, the progress information relevant to the fertile ovum F selected by the fertile ovum transplanter from the second terminal 40, is transmitted to the acquisition unit 24 through the network N.

Then, the acquisition unit 24 acquiring the progress information, outputs the progress information to the analysis unit 25, the output unit 26, and the storage unit 28. The output unit 26 acquiring the progress information from the acquisition unit 24 outputs the progress information to the fertile ovum quality evaluator (the first terminal 30). In addition, the progress information output to the storage unit 28, is stored in the storage unit 28.

Here, the acquisition unit 24 of this embodiment acquires at least one of transplant information, propagation information, fattening information, and meat information, relevant to the fertile ovum F selected on the basis of the evaluation support information (the first fertile ovum analysis information and the identification information) and the fertile ovum evaluation information, as the progress information.

The transplant information, for example, is information relevant to an eclosion rate, an implantation rate, a fetation rate, a fecundation rate, an abortion rate, a birthrate, and the like, which are known by transplanting the selected fertile ovum F to the livestock.

The propagation information, for example, is information relevant to a propagation rate, a survival rate, a malformation rate, an average survival age, a prevalence rate, a morbidity rate, and the like, which are known by growing the selected fertile ovum F to the imago, and by propagating species of the same blood by using the imago as parents.

The fattening information, for example, is information relevant to the weight, the height, and the health condition of the imago, which are known by growing the selected fertile ovum F to the immatures, and by artificially fattening the immatures to the imago, information relevant to the price at the time of selling the fattened immatures or imago by auction, or the like.

The meat information, for example, is information relevant to a meat quality grade, a yield grade, and delicious taste of the meat, which are known by growing the selected fertile ovum F to the imago, and by performing meat processing with respect to the imago, information relevant to the price at the time of selling the meat in the market, or the like.

Note that "Transplant Information", "Propagation Information", "Fattening Information", and "Meat Information", described above, are the same in the following description.

Subsequently, the analysis unit 25 acquiring the progress information from the acquisition unit 24 reads out at least one of the shape information, the motion information, the compaction information, the contraction information, the expansion information, the dormant information, the growing information according to findings, the quality information, the identification information, and the culture environment information, which are stored in the storage unit 28, and are relevant to the fertile ovum F associated with the progress information, from the storage unit 28.

Next, the analysis unit 25 installs the information read out from the progress information and the storage unit 28 in the algorithm set in advance, as the learning data, and thus, builds out again the identifier. Accordingly, the identifier is updated.

On the other hand, the progress information is displayed on the first terminal 30 acquiring the progress information from the output unit 26. That is, the progress information relevant to the fertile ovum F selected on the basis of the evaluation support information (the first fertile ovum analysis information and the identification information) and the fertile ovum evaluation information, is notified to the fertile ovum quality evaluator. Accordingly, when the fertile ovum quality evaluator evaluates the quality of the fertile ovum F on the basis of the evaluation support information (the fertile ovum analysis report), it is possible to perform the quality evaluation also considering the progress information.

<Operation>

Recently, in the field of a fertilization treatment, the animal industry, or the like, the quality of the fertile ovum to be transplanted is an important factor affecting a transplant record. In the identification of the fertile ovum to be transplanted, it is general that the growing condition or the quality of the fertile ovum are determined according to morphological findings using an optical microscope, an image processing apparatus, or the like.

However, in the quality evaluation of the fertile ovum before the transplant, a morphological evaluation method as described above tends not only to be skilled, but also to be easily subjective. For this reason, recently, it has been desirable to acquire a quality evaluation result of the fertile ovum evaluated with a higher degree of accuracy compared to the morphological findings, in order to select a good fertile ovum.

In particular, in the livestock industry where a process of collecting a plurality of fertile ova from a uterus of a cow, of identifying normal fertile ova from the plurality of fertile ova, and of transplanting the fertile ova into a uterus of a cow different from the cow from which the fertile ova are collected, is performed several times, the number of times of parturition for life of the cow is limited, and thus, an adverse effect in a case where an imago derived from the fertile ovum selected according to the morphological findings does not have desired quality, increases.

Accordingly, in the current livestock industry, a quality evaluation result analyzed with a higher degree of accuracy such as to which degree of development potential the fertile ovum before the transplant presents after the transplant, is required from the viewpoint of improving productivity, in order to treat the livestock as a commercial product.

However, in the current livestock industry, in order to obtain a quality evaluation result of the fertile ovum before the transplant is analyzed with a high degree of accuracy, there is no way but to ask a specialized institution or to ask an expert such as a skilled embryologist, and in a case of asking, not only does it take more time than necessary until an analysis result is obtained, but also it costs too much until the fertile ovum having desired quality is obtained.

In consideration of such circumstances, in the fertile ovum quality evaluation system 100 according to this embodiment, the analysis information of the plurality of observation images in which the fertile ova F are captured in chronological order along the culturing time, analyzed with a high degree of accuracy according to the specialized AI, and the evaluation information of the analysis information evaluated by the fertile ovum quality evaluator, are can be transmitted to the second terminal 40 of the fertile ovum transplanter.

Accordingly, the fertile ovum transplanter is capable of easily acquiring the quality evaluation result relevant to the fertile ovum F which is analyzed?evaluated with a greatly high degree of accuracy without selecting a place, compared to a quality evaluation method according to the morphological findings. Accordingly, as with the related art, it is possible to not only save the labor of asking the specialized institution or the embryologist for the quality evaluation of the fertile ovum, but also reduce the cost.

In addition, in the fertile ovum quality evaluation system 100, the fertile ovum transplanter inputs the acquisition request and the purchase request, based on the evaluation support information (the first fertile ovum analysis information and the identification information) and the fertile ovum evaluation information, into the second terminal 40.

Accordingly, the fertile ovum transplanter is capable of selecting and obtaining only a fertile ovum having desired quality, for example, fertile ovum having a high probability of being grown to high-quality livestock after the transplant, with reference to the analysis result analyzed with a high degree of accuracy according to the specialized AI, and the evaluation information of the analysis result evaluated by the fertile ovum quality evaluator.

Accordingly, not only is the efficiency of the selecting operation of selecting the fertile ovum of which the development potential after the transplant is expected to be high improved, but also the risk of selecting a fertile ovum becomes an imago having desired quality is extremely suppressed.

Further, in the fertile ovum quality evaluation system 100 according to this embodiment, a process from the analysis of the observation image of the fertile ovum F, to the transmission of the progress information with respect to the information processing apparatus 20 and the first terminal 30 from the fertile ovum transplanter, is completed in one system. Accordingly, the fertile ovum transplanter is capable of transmitting the acquisition request or the purchase request to the information processing apparatus 20 through the second terminal 40 at any time, without depending on the place and the time. Accordingly, convenience of the selecting operation for selecting the fertile ovum F is improved.

Second Embodiment

Figure 14:
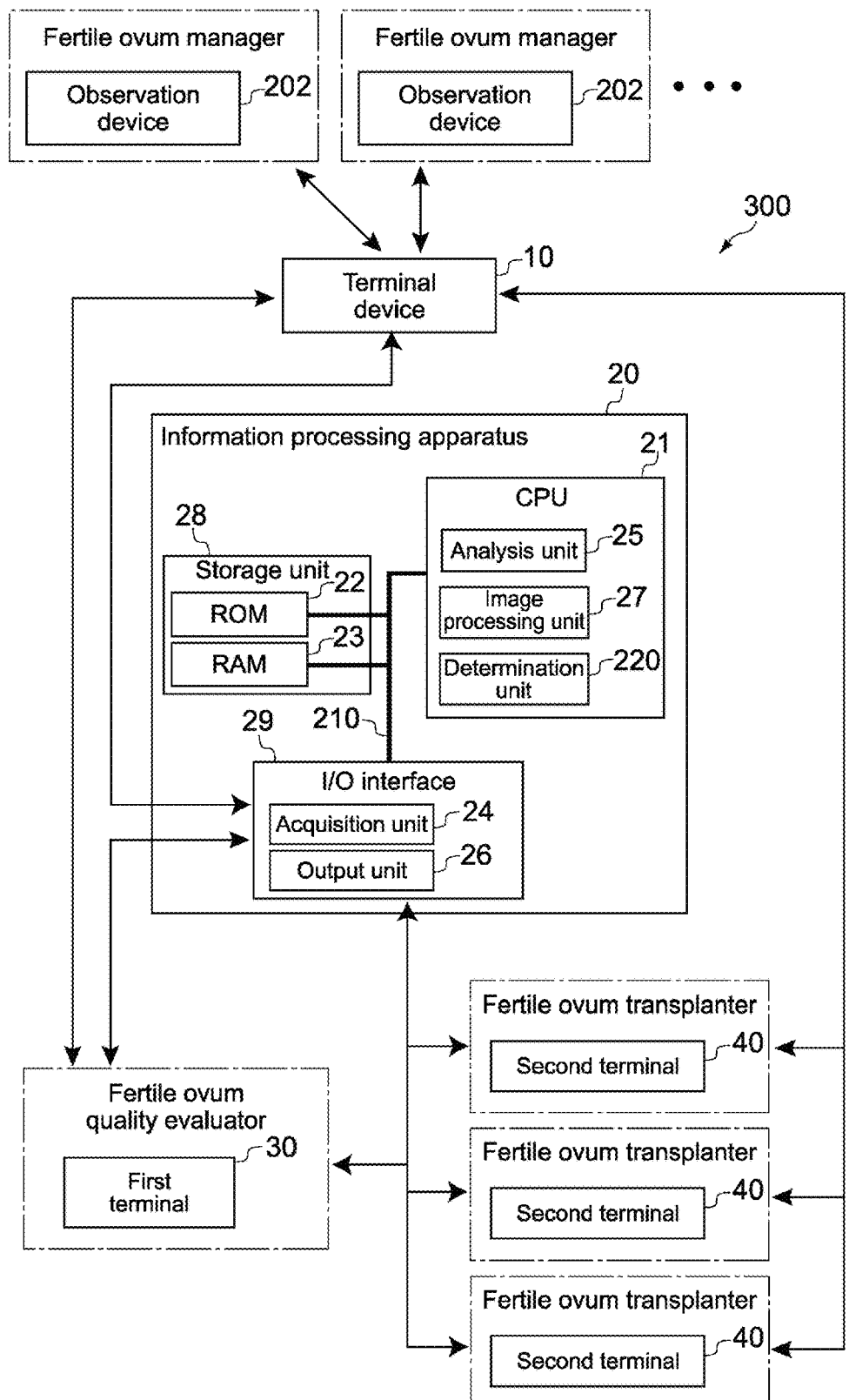
FIG. 14 is a block diagram of a fertile ovum quality evaluation system according to a second embodiment of the present technology.

FIG. 14 is a block diagram of a fertile ovum quality evaluation system 300 according to a second embodiment of the present technology. Hereinafter, the same reference numerals will be applied to the same constituents as those of the first embodiment, and the detailed description thereof will be omitted.

As illustrated in FIG. 13, the fertile ovum quality evaluation system 300 according to this embodiment is different from the first embodiment in that the information processing apparatus 20 further includes a determination unit 220, and is connected to a plurality of second terminals 40 through the network N such that communication can be performed with each other.

The determination unit 220 of this embodiment determines to which purchase request of the purchase requests acquired from each of the plurality of second terminals 40 the process responds. The detailed function of the determination unit 220 will be described below.

<Fertile Ovum Quality Evaluation Method>

Figure 15:
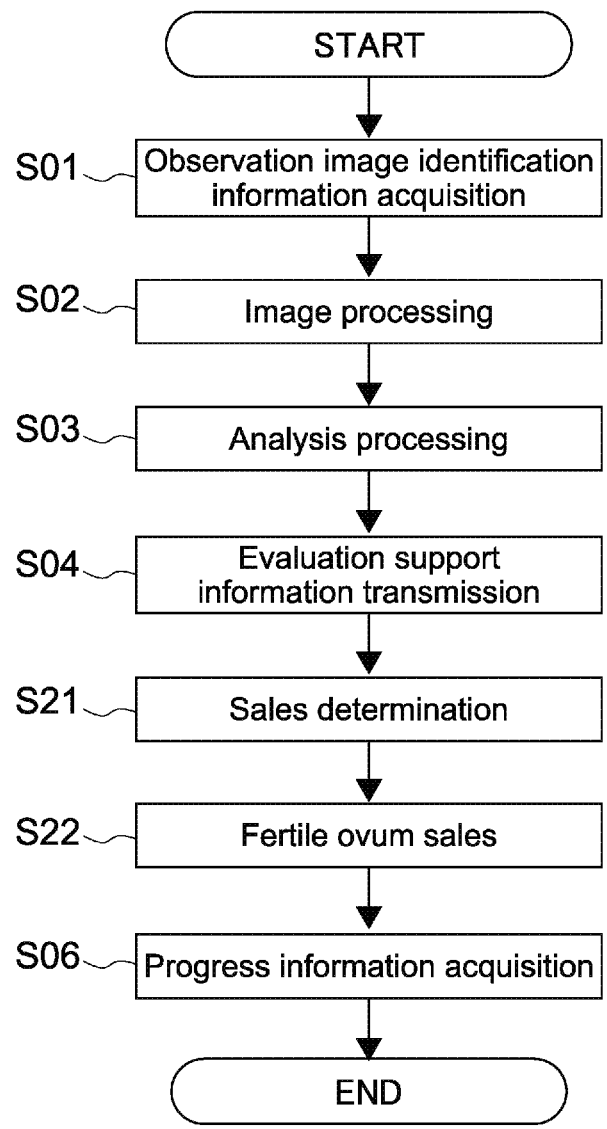
FIG. 15 is a flowchart illustrating a method of evaluating quality of a fertile ovum of the fertile ovum quality evaluation system.

FIG. 15 is a flowchart illustrating a method of evaluating the quality of the fertile ovum F of the fertile ovum quality evaluation system 300 according to this embodiment. Hereinafter, the quality evaluation method of the fertile ovum F will be described while suitably referring to FIG. 15. Note that the description of the same steps as those of the first embodiment will be omitted.

The fertile ovum quality evaluation system 300 according to this embodiment is an auction system of selling the fertile ovum F to the fertile ovum transplanter presenting the most excellent purchase condition, on the basis of the evaluation support information (the first fertile ovum analysis information and the identification information) and the fertile ovum evaluation information, relevant to the fertile ovum F. Hereinafter, the details will be described.

(Step S21: Sales Determination)

The fertile ovum quality evaluator transmits the evaluation support information (the first fertile ovum analysis information and the identification information) and the fertile ovum evaluation information, relevant to the fertile ovum F, to each of the plurality of second terminals 40, through the first terminal 30.

Each of the fertile ovum transplanters inputs the purchase request of purchasing the fertile ovum F into the second terminal 40, on the basis of the evaluation support information and the fertile ovum evaluation information, displayed on the second terminal 40. In this embodiment, for example, the desired number of purchased fertile ova such as how many fertile ova F the fertile ovum quality evaluator purchases, the purchase price set by the fertile ovum transplanter, on the basis of the evaluation support information and the fertile ovum evaluation information, and the like are input into the second terminal 40, as the purchase request.

The plurality of second terminals 40 into which the purchase request is input from the fertile ovum transplanter, transmits the purchase request to the acquisition unit 24 through the network N. The acquisition unit 24 outputs the purchase request acquired from each of the plurality of second terminals 40, to the determination unit 220.

The determination unit 220 determines to which purchase request of the purchase requests of each of the plurality of second terminals 40 output from the acquisition unit 24 the process responds. At this time, typically, the determination unit 220 receives only the purchase request from the second terminal 40 of the fertile ovum transplanter with the highest purchase price, in the purchase requests transmitted from the plurality of second terminals 40, and outputs the purchase request to the output unit 26.

(Step S22: Fertile Ovum Sales)

Subsequently, the output unit 26 transmits the sales command according to the purchase request from the second terminal 40 of the fertile ovum transplanter allowed to purchase the fertile ovum, to the first terminal 30 of the fertile ovum quality evaluator producing the auctioned fertile ovum F, through the network N. The sales command is a command of allowing the fertile ovum transplanter to accelerate the sales of the fertile ovum F by taking out the fertile ovum F bought by the fertile ovum transplanter, from the well W.

Next, the fertile ovum quality evaluator receives the fact that the first terminal 30 receives the sales command from the output unit 26, and transmits the sales command to the gateway terminal 10a through the network N. Then, the gateway terminal 10a receiving the sales command from the first terminal 30, outputs the sales command to the control recording PC 205.

The control recording PC 205 into which the sales command is input, displays the information according to the sales command, on the display device 206. Accordingly, the sales command according to the purchase request of the fertile ovum transplanter is notified to the fertile ovum manager managing the fertile ovum F. Then, the fertile ovum manager to which the sales command is notified, performs the shipping and delivery of the fertile ovum F bought by the fertile ovum transplanter, on the basis of the purchase request of the fertile ovum transplanter allowed to purchase the fertile ovum.

Next, in a case where the fertile ovum transplanter receives the fertile ovum F bought by himself from the fertile ovum manager, the fertile ovum quality evaluator pays the price based on the purchase price set by himself, input into the second terminal 40. The payment of the fertile ovum transplanter buying the fertile ovum F with respect to the fertile ovum quality evaluator may be performed by mail or through bank transfer, or may be executed by online payment using a dedicated application for a fertile ovum transplanter, which is installed in the second terminal 40.

<Operation>

In the fertile ovum quality evaluation system 300 of this embodiment, fertile ovum F is bought by the fertile ovum transplanter with the highest purchase price, on the basis of the evaluation support information (the first fertile ovum analysis information and the identification information) and the fertile ovum evaluation information, relevant to the fertile ovum F. Accordingly, profitability for the fertile ovum quality evaluator to produce the fertile ovum F as the business, is dramatically improved.

Modification Example

As illustrated in FIG. 13, the fertile ovum quality evaluation system 300 of this embodiment is configured such that a single first terminal 30 is connected to the plurality of second terminals 40 through the network N, but is not limited thereto.

For example, the plurality of first and second terminals 30 and 40 may be connected to each other through the network N, or the plurality of first terminals 30 may be connected to a single second terminal 40 through the network N. Alternatively, a single first terminal 30 and a single second terminal 40 may be connected to each other through the network N.

Third Embodiment

Figure 16:
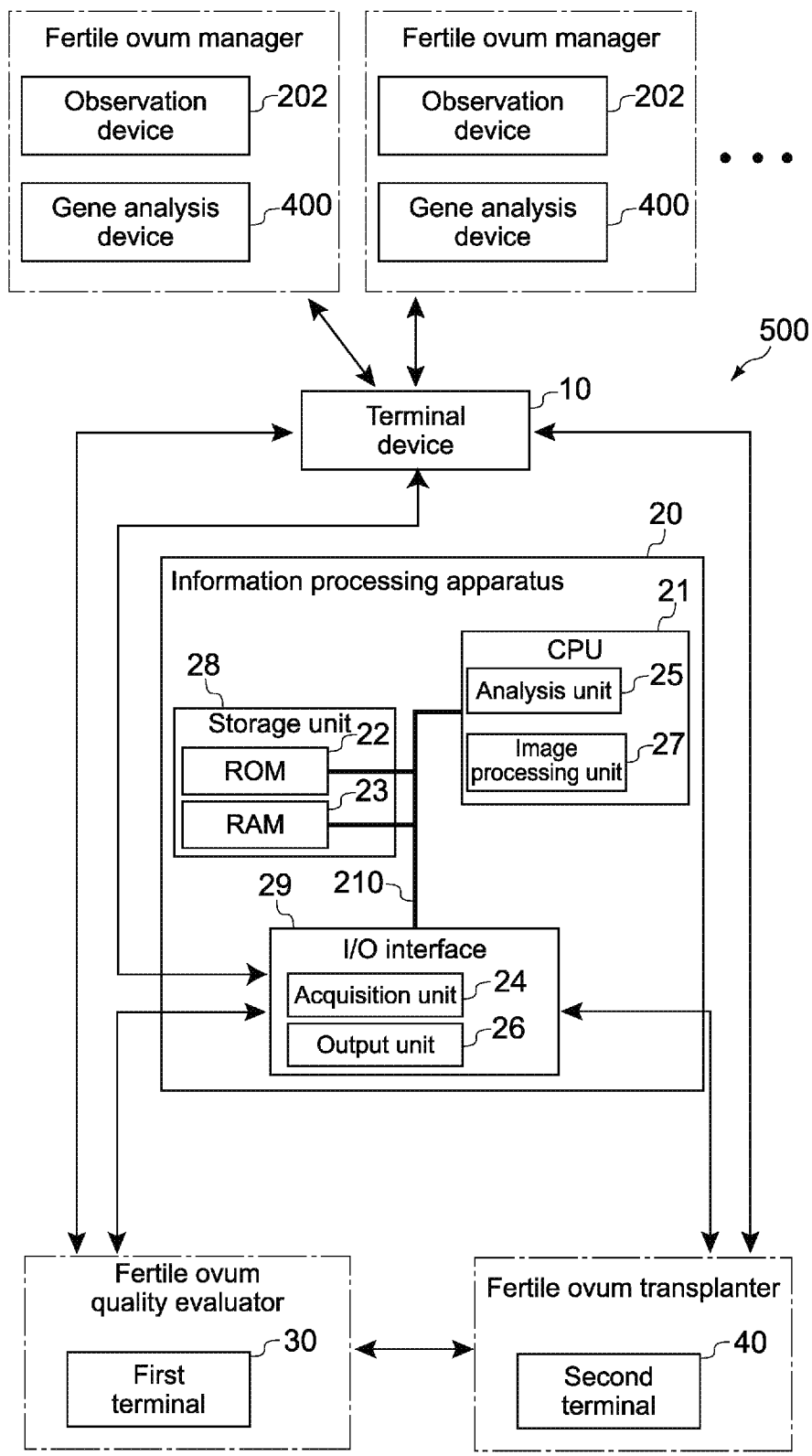
FIG. 16 is a block diagram of a fertile ovum quality evaluation system according to a third embodiment of the present technology.

FIG. 16 is a block diagram of a fertile ovum quality evaluation system 500 according to a third embodiment of the present technology. Hereinafter, the same reference numerals will be applied to the same constituents as those of the first embodiment, and the detailed description thereof will be omitted.

As illustrated in FIG. 16, the fertile ovum quality evaluation system 500 of this embodiment is different from the first embodiment in that the fertile ovum manager handles not only the observation device 202 but also a gene analysis device 400.

The gene analysis device 400 is connected to the control recording PC 205, and is connected to the gateway terminal 10a through the control recording PC 205. That is, the gene analysis device 400 is connected to the information processing apparatus 20, and the first and second terminals 30 and 40 through the control recording PC 205 and the gateway terminal 10a such that communication can be performed with each other.

The gene analysis device 400 of this embodiment, for example, is a gene analysis device using a deoxyribonucleic acid (DNA) chip, a DNA sequencing method or a polymerase chain reaction (PCR) method, or the like, but is not limited thereto.

In addition, gene analysis information obtained by the gene analysis device 400 by analyzing the gene of the fertile ovum F, for example, is information relevant to a base sequence of four types of adenine (A), thymine (T), guanine (G), cytosine (C), which is obtained by single nucleotide polymorphism (SNP) typing, and the same applies to the following description.

<Fertile Ovum Quality Evaluation Method>

Figure 17:
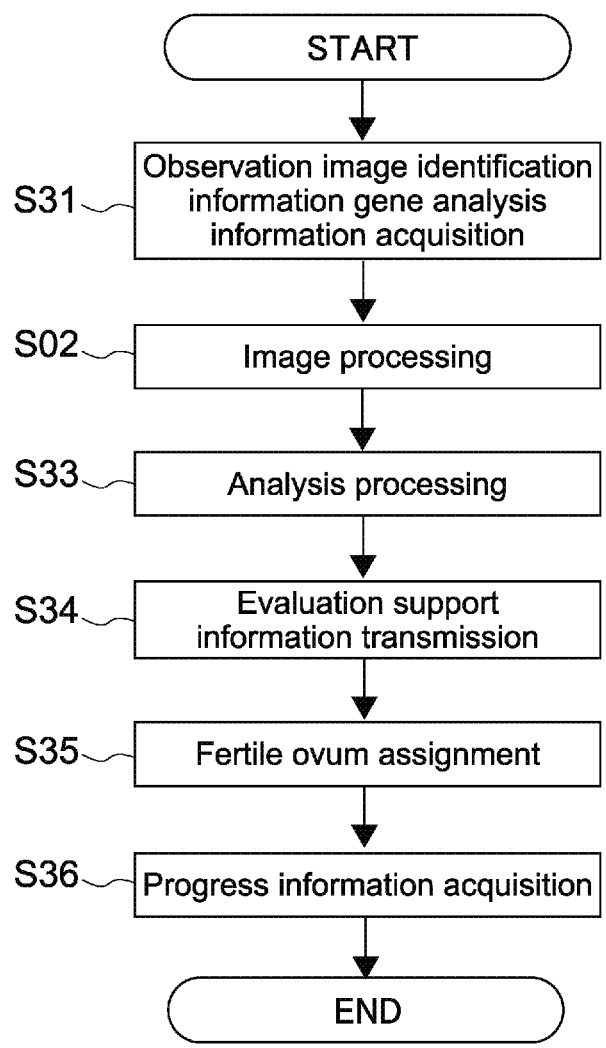
FIG. 17 is a flowchart illustrating a method of evaluating quality of a fertile ovum of the fertile ovum quality evaluation system.

FIG. 17 is a flowchart illustrating a method of evaluating the quality of the fertile ovum F of the fertile ovum quality evaluation system 500 of this embodiment. Hereinafter, the quality evaluation method of the fertile ovum F will be described, while suitably referring to FIG. 17. Note that the description of the same steps as those of the first embodiment will be omitted.

(Step S31: Observation Image?Identification Information?Gene Analysis Information Acquisition) First, the identification information relevant to the fertile ovum F, and the gene analysis information obtained by the gene analysis device 400 by analyzing the gene of the fertile ovum F, are input into the control recording PC 205. The identification information and the gene analysis information input into the control recording PC 205, are stored in the control recording PC 205, and are transmitted to the gateway terminal 10a. The gateway terminal 10a receiving the identification information and the gene analysis information, transmits the information to the acquisition unit 24 through the network N, and the acquisition unit 24 acquires the information.

Subsequently, the output unit 26 receives the fact that the acquisition unit 24 acquires the identification information and the gene analysis information from the gateway terminal 10a through the network N, and transmits the capturing command of capturing the fertile ovum F to the gateway terminal 10a through the network N. The gateway terminal 10a receiving the capturing command transmits the capturing command to the control recording PC 205.

The control recording PC 205 receiving the capturing command, controls the capturing unit 2021 according to the capturing command. Accordingly, as described in the first embodiment, the first time-lapse image G1 including six fertile ova F is generated, and the first time-lapse image G1 is transmitted to the control recording PC 205.

The control recording PC 205 into which the first time-lapse image G1 is input, transmits the first time-lapse image G1 to the gateway terminal 10a. The gateway terminal 10a receiving the first time-lapse image G1, transmits the first time-lapse image G1 to the acquisition unit 24 through the network N, and the acquisition unit 24 acquires the first time-lapse image G1.

The acquisition unit 24 outputs the first time-lapse image G1, the identification information, and the gene analysis information, which are acquired from the gateway terminal 10a through the network N, to the storage unit 28, and the information is stored in the storage unit 28. In addition, the acquisition unit 24 outputs the acquired first time-lapse image G1 to the image processing unit 27, and outputs the identification information and the gene analysis information to the output unit 26.

(Step S33: Analysis Processing)

The analysis unit 25 reads out at least one of the shape information, the motion information, the compaction information, the contraction information, the expansion information, the dormant information, the growing information according to findings, and the quality information, based on the gene analysis information of the fertile ova collected from the plurality of fertile ova managers through the network N, and the time-lapse images of the fertile ova, which are stored in advance in the storage unit 28, from the storage unit 28. Such information corresponds to "Learning Data" of FIG. 13.

Next, the analysis unit 25 builds out an identifier by installing the learning data read out from the storage unit 28 in an algorithm set in advance. Accordingly, the analysis unit 25 includes the identifier.

Note that the algorithm corresponds to "Algorithm" of FIG. 13, and for example, functions as the machine learning algorithm described in the first embodiment. In addition, the identifier corresponds to "Learned Model" of FIG. 13.

Next, the analysis unit 25 generates second fertile ovum analysis information by applying the identifier built out as described above, to the second time-lapse image G2 output from the image processing unit 27, and the gene analysis information relevant to the fertile ovum F associated with the second time-lapse image G2.

Specifically, the second time-lapse image and the gene analysis information are subjected to the deep learning analysis by the identifier, and thus, the second fertile ovum analysis information is generated. Then, the analysis unit 25 outputs the second fertile ovum analysis information to the output unit 26 and the storage unit 28, and the second fertile ovum analysis information is stored in the storage unit 28.

Note that the second time-lapse image G2, and the gene analysis information relevant to the fertile ovum F associated with the second time-lapse image G2, correspond to "Input Data" of FIG. 13, and the second fertile ovum analysis information corresponds to "Output" of FIG. 13.

(Step S34: Evaluation Support Information Transmission)

The output unit 26 generates the evaluation support information including at least the identification information and the gene analysis information, acquired from the acquisition unit 24, and the second fertile ovum analysis information acquired from the analysis unit 25. Then, the output unit 26 outputs the evaluation support information to the fertile ovum quality evaluator through the network N.

The evaluation support information, for example, is transmitted to the first terminal 30 as "Fertile Ovum Analysis Report" for a fertile ovum quality evaluator. "Fertile Ovum Analysis Report", for example, may be displayed on the first terminal 30 through application software for a fertile ovum quality evaluator, which is installed in the first terminal 30.

The first terminal 30 receiving the evaluation support information, for example, displays the evaluation support information on the web browser, as the WEB dashboard. Accordingly, the quality evaluation of the fertile ovum F according to the fertile ovum quality evaluator, is supported. Specifically, the fertile ovum evaluation information based on the evaluation support information is input into the first terminal 30, according to the fertile ovum quality evaluator evaluating?browsing the evaluation support information (the fertile ovum analysis report) displayed on the first terminal 30.

(Step S35: Fertile Ovum Assignment)

The first terminal 30 transmits the evaluation support information acquired from the output unit 26 (the second fertile ovum analysis information, the identification information, and the gene analysis information), and the fertile ovum evaluation information input by the fertile ovum quality evaluator, to the second terminal 40 through the network N.

Such information transmitted to the second terminal 40, for example, is transmitted to the second terminal 40 as "Fertile Ovum Analysis?Evaluation Report" for a fertile ovum transplanter. "Fertile Ovum Analysis?Evaluation Report", for example, may be displayed on the second terminal 40 through application software for a fertile ovum transplanter, which is installed in the second terminal 40.

The second terminal 40 acquiring the evaluation support information (the second fertile ovum analysis information, the identification information, and the gene analysis information) and the fertile ovum evaluation information, for example, displays the information on the web browser, as the WEB dashboard. Accordingly, the fertile ovum transplanter is capable of selecting the fertile ovum F having desired quality, with reference to the fertile ovum analysis?evaluation report (the evaluation support information and the fertile ovum evaluation information), and the selecting operation of the fertile ovum F is supported by the fertile ovum transplanter.

Subsequently, the fertile ovum transplanter inputs the acquisition request of acquiring the fertile ovum F, to the second terminal 40 through the input unit 40b, on the basis of the evaluation support information (the second fertile ovum analysis information, the identification information, and the gene analysis information) and the fertile ovum evaluation information, displayed on the second terminal 40.

The second terminal 40 into which the acquisition request is input from the fertile ovum transplanter, transmits the acquisition request to the acquisition unit 24 through the transmitting unit 40c, through the network N. Next, the output unit 26 receives the fact that the acquisition unit 24 acquires the acquisition request from the second terminal 40, and outputs the assignment command according to the acquisition request to the first terminal 30 through the network N.

Next, the fertile ovum quality evaluator receives the fact that the first terminal 30 receives the assignment command from the output unit 26, and transmits the assignment command to the gateway terminal 10a through the network N. Then, the gateway terminal 10a receiving the assignment command from the first terminal 30, outputs the assignment command to the control recording PC 205.

The control recording PC 205 into which the assignment command is input, displays the information according to the assignment command, through the display device 206. Accordingly, the assignment command according to the acquisition request of the fertile ovum transplanter is notified to the fertile ovum manager managing the fertile ovum F. Then, the fertile ovum manager to which the assignment command is notified, performs the shipping and delivery of the fertile ovum F selected by the fertile ovum transplanter, on the basis of the acquisition request of the fertile ovum transplanter.

(Step S36: Progress Information Acquisition)

The fertile ovum transplanter transplants the fertile ovum F which is shipped and delivered from the fertile ovum manager, to the livestock, and performs the parturition and the propagation. Then, the immatures generated from the livestock are grown to the imago, and the imago is sold in the market. The fertile ovum transplanter obtains the progress information relevant to the fertile ovum F selected by himself, on the basis of the evaluation support information (the second fertile ovum analysis information, the identification information, and the gene analysis information) and the fertile ovum evaluation information, while the fertile ovum F assigned from the fertile ovum manager is grown to the imago to be sold.

Next, the fertile ovum transplanter inputs the progress information obtained as described above, to the second terminal 40. Accordingly, the progress information relevant to the fertile ovum F selected by the fertile ovum transplanter from the second terminal 40, is transmitted to the acquisition unit 24 through the network N.

Then, the acquisition unit 24 acquiring the progress information, outputs the progress information to the analysis unit 25, the output unit 26, and the storage unit 28. The output unit 26 acquiring the progress information from the acquisition unit 24, outputs the progress information to the fertile ovum quality evaluator (the first terminal 30). In addition, the progress information output to the storage unit 28, is stored in the storage unit 28.

Here, the acquisition unit 24 of this embodiment, acquires at least one of the transplant information, the propagation information, the fattening information, and the meat information, relevant to the fertile ovum F selected on the basis of the evaluation support information (the second fertile ovum analysis information, the identification information, and the gene analysis information) and the fertile ovum evaluation information, as the progress information.

Subsequently, the analysis unit 25 acquiring the progress information from the acquisition unit 24, reads out the shape information, the motion information, the compaction information, the contraction information, the expansion information, the dormant information, the growing information according to findings, the quality information, the gene analysis information, and the culture environment information, relevant to the fertile ovum F associated with the progress information, which are stored in the storage unit 28, from the storage unit 28.

Next, the analysis unit 25 installs the progress information and the information read out from the storage unit 28 in the algorithm set in advance, as the learning data, and thus, builds out again the identifier. Accordingly, the identifier is updated.

On the other hand, the first terminal 30 acquiring the progress information from the acquisition unit 24, displays the progress information. That is, the progress information relevant to the fertile ovum F selected on the basis of the evaluation support information (the second fertile ovum analysis information, the identification information, and the gene analysis information) and the fertile ovum evaluation information, is notified to the fertile ovum quality evaluator. Accordingly, when the fertile ovum quality evaluator evaluates the quality of the fertile ovum F on the basis of the evaluation support information (the fertile ovum analysis report), it is possible to perform the quality evaluation also considering the progress information.

<Operation>

In the fertile ovum quality evaluation system 500 according to this embodiment, the acquisition request based on the evaluation support information (the second fertile ovum analysis information, the identification information, and the gene analysis information) and the fertile ovum evaluation information is input into the second terminal 40 by the fertile ovum transplanter.

Accordingly, the fertile ovum transplanter is capable of selecting and obtaining the fertile ovum F having desired quality, with reference to an analysis result of the second time-lapse image G2, and the gene analysis information relevant to the fertile ovum F associated with the second time-lapse image G2, which are analyzed with a high degree of accuracy by the specialized AI, the evaluation information of the analysis result further evaluated by the fertile ovum quality evaluator, and the identification information relevant to the fertile ovum F.

Fourth Embodiment

Figure 18:
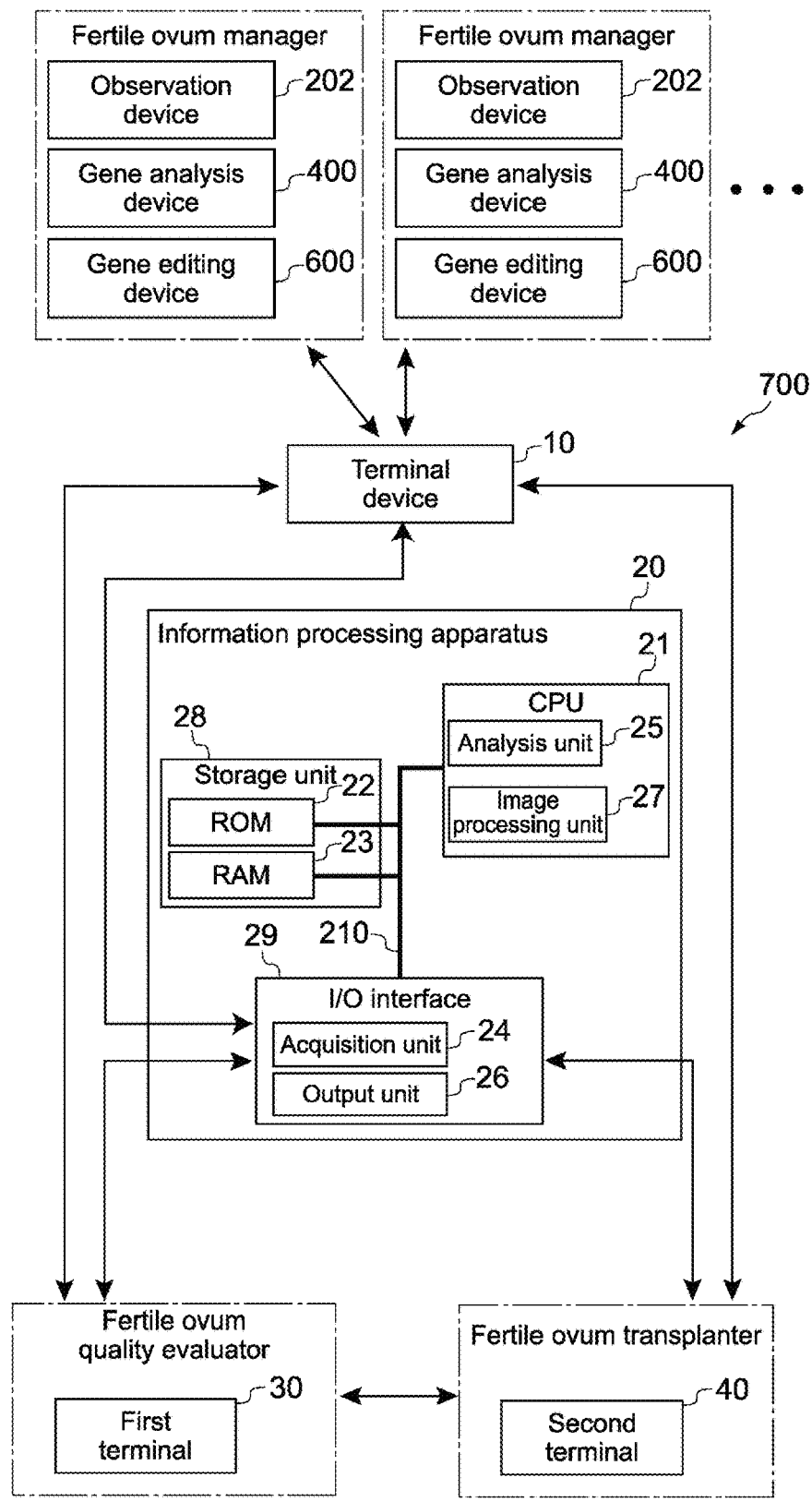
FIG. 18 is a block diagram of a fertile ovum quality evaluation system according to a fourth embodiment of the present technology.

FIG. 18 is a block diagram of a fertile ovum quality evaluation system 700 according to a fourth embodiment of the present technology. Hereinafter, the same reference numerals will be applied to the same constituents as those of the first embodiment and the third embodiment, and the detailed description thereof will be omitted.

As illustrated in FIG. 18, the fertile ovum quality evaluation system 700 of this embodiment is different from the first embodiment and the third embodiment in that the fertile ovum manager handles not only the observation device 202, but also a gene editing device 600.

The gene editing device 600 is connected to the control recording PC 205, and is connected to the gateway terminal 10a through the control recording PC 205. That is, the gene editing device 600 is connected to the information processing apparatus 20 and the first and second terminals 30 and 40 through the control recording PC 205 and the gateway terminal 10a, such that communication can be performed with each other.

The gene editing device 600 is an arbitrary gene editing tool editing genome information of the fertile ovum F, and examples of such a gene editing tool include clustered regularly interspaced short palindromic repeats/CRISPR-associated protein9 (CRISPER/Cas9) and the like.

In addition, gene editing information obtained by editing the gene of the fertile ovum F by the gene editing device 600, for example, is genome editing information obtained by changing a DNA sequence of the fertile ovum F, and the same applies to the following description.

<Fertile Ovum Quality Evaluation Method>

Figure 19:
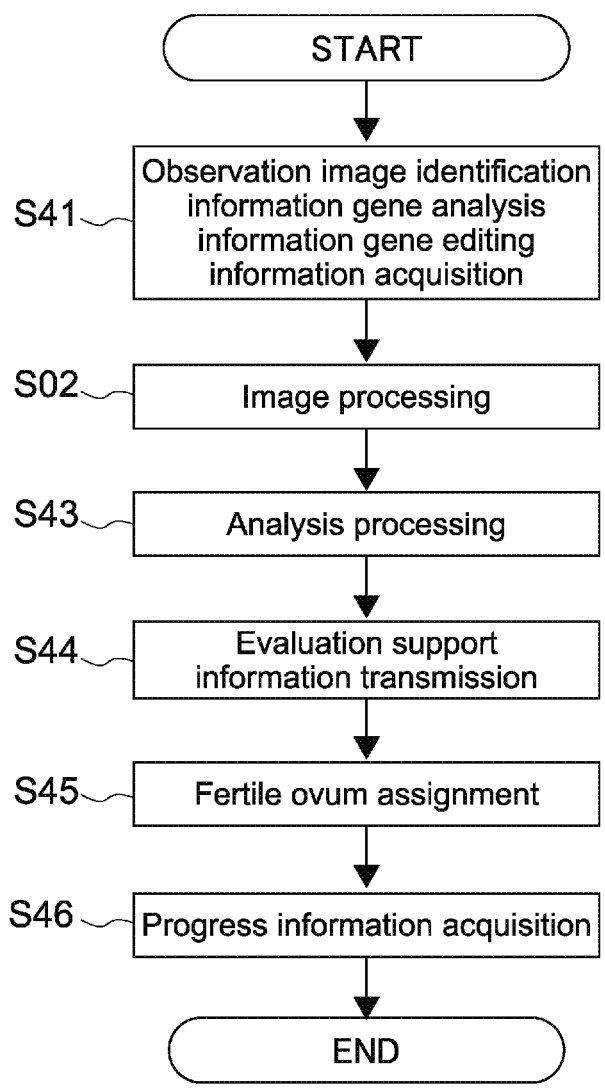
FIG. 19 is a flowchart illustrating a method of evaluating quality of a fertile ovum of the fertile ovum quality evaluation system.

FIG. 19 is a flowchart illustrating a method of evaluating the quality of the fertile ovum F of the fertile ovum quality evaluation system 700 according to this embodiment. Hereinafter, the quality evaluation method of the fertile ovum F will be described while suitably referring to FIG. 19. Note that the description of the same steps as those of the first embodiment will be omitted.

(Step S41: Observation Image?Identification Information Acquisition?Gene Analysis Information?Gene Editing Information)

First, the identification information and the gene analysis information, relevant to the fertile ovum F, and the gene editing information obtained by editing the gene of the fertile ovum F by the gene editing device 600, are input into the control recording PC 205. The identification information, the gene analysis information, and the gene editing information input into the control recording PC 205, are stored in the control recording PC 205, and are transmitted to the gateway terminal 10a. The gateway terminal 10a receiving the identification information, the gene analysis information, and the gene editing information, transmits the information to the acquisition unit 24 through the network N, and the acquisition unit 24 acquires the information.

Subsequently, the output unit 26 receives the fact that the acquisition unit 24 acquires the identification information, the gene analysis information, and the gene editing information from the gateway terminal 10a through the network N, and transmits the capturing command of capturing the fertile ovum F to the gateway terminal 10a through the network N. The gateway terminal 10a receiving the capturing command, outputs the capturing command to the control recording PC 205.

The control recording PC 205 receiving the capturing command, controls the capturing unit 2021 according to the capturing command. Accordingly, as described in the first embodiment, the first time-lapse image G1 including six fertile ova F is generated, and the first time-lapse image G1 is transmitted to the control recording PC 205.

The control recording PC 205 into which the first time-lapse image G1 is input, transmits the first time-lapse image G1 to the gateway terminal 10a. The gateway terminal 10a receiving the first time-lapse image G1, transmits the first time-lapse image G1 to the acquisition unit 24 through the network N, and the acquisition unit 24 acquires the first time-lapse image G1.

The acquisition unit 24 outputs the first time-lapse image G1, the identification information, the gene analysis information, and the gene editing information, which are acquired from the gateway terminal 10a through the network N, to the storage unit 28, and the information is stored in the storage unit 28. In addition, the acquisition unit 24 outputs the acquired first time-lapse image G1 to the image processing unit 27, and outputs the identification information, the gene analysis information, and the gene editing information to the output unit 26.

(Step S43: Analysis Processing)

The analysis unit 25 reads out at least one of the shape information, the motion information, the compaction information, the contraction information, the expansion information, the dormant information, the growing information according to findings, and the quality information, based on the gene analysis information, the gene editing information of the fertile ova collected from the plurality of fertile ova managers through the network N, and the time-lapse images of the fertile ova, which are stored in advance in the storage unit 28, from the storage unit 28. Such information corresponds to "Learning Data" of FIG. 13.

Next, the analysis unit 25 builds out an identifier by installing the learning data read out from the storage unit 28 in an algorithm set in advance. Accordingly, the analysis unit 25 includes the identifier.

Note that the algorithm corresponds to "Algorithm" of FIG. 13, and for example, functions as the machine learning algorithm as described in the first embodiment. In addition, the identifier corresponds to "Learned Model" of FIG. 13.

Next, the analysis unit 25 generates third fertile ovum analysis information by applying the identifier built out as described above, to the second time-lapse image G2 output from the image processing unit 27, and the gene analysis information and the gene editing information, relevant to the fertile ovum F associated with the second time-lapse image G2. Then, the analysis unit 25 outputs the third fertile ovum analysis information to the output unit 26 and the storage unit 28, and the third fertile ovum analysis information is stored in the storage unit 28.

Note that the second time-lapse image G2, and the gene analysis information and the gene editing information, relevant to the fertile ovum F associated with the second time-lapse image G2, correspond to "Input Data" of FIG. 13, and the third fertile ovum analysis information corresponds to "Output" of FIG. 13.

(Step S44: Evaluation Support Information Transmission)

The output unit 26 generates the evaluation support information including at least the identification information, the gene analysis information, and the gene editing information, acquired from the acquisition unit 24, and the third fertile ovum analysis information acquired from the analysis unit 25. Then, the output unit 26 transmits the evaluation support information to the fertile ovum quality evaluator through the network N.

The evaluation support information, for example, is transmitted to the first terminal 30, as "Fertile Ovum Analysis Report" for a fertile ovum quality evaluator. "Fertile Ovum Analysis Report", for example, may be displayed on the first terminal 30 through application software for a fertile ovum quality evaluator, which is installed in the first terminal 30.

The first terminal 30 receiving the evaluation support information, for example, displays the evaluation support information on the web browser, as the WEB dashboard. Accordingly, the quality evaluation of the fertile ovum F is supported by the fertile ovum quality evaluator. Specifically, the fertile ovum evaluation information based on the evaluation support information is input into the first terminal 30 by the fertile ovum quality evaluator evaluating?browsing the evaluation support information displayed on the first terminal 30 (the fertile ovum analysis report).

(Step S45: Fertile Ovum Assignment)

The first terminal 30 transmits the evaluation support information acquired from the output unit 26 (the third fertile ovum analysis information, the identification information, the gene analysis information, and the gene editing information), and the fertile ovum evaluation information input by the fertile ovum quality evaluator, to the second terminal 40 through the network N.

The information transmitted to the second terminal 40, for example, is transmitted to the second terminal 40, as "Fertile Ovum Analysis?Evaluation Report" for a fertile ovum transplanter. "Fertile Ovum Analysis?Evaluation Report", for example, may be displayed on the second terminal 40 through application software for a fertile ovum transplanter, which is installed in the second terminal 40.

The second terminal 40 acquiring the evaluation support information (the third fertile ovum analysis information, the identification information, the gene analysis information, and the gene editing information) and the fertile ovum evaluation information, for example, displays the information on the web browser, as the WEB dashboard. Accordingly, the fertile ovum transplanter is capable of selecting the fertile ovum having desired quality, with reference to the fertile ovum analysis?evaluation report (the evaluation support information and the fertile ovum evaluation information), and the selecting operation of the fertile ovum is supported by the fertile ovum transplanter.

Subsequently, the fertile ovum transplanter inputs the acquisition request of acquiring the fertile ovum F, into the second terminal 40 through the input unit 40b, on the basis of the evaluation support information (the third fertile ovum analysis information, the identification information, the gene analysis information, and the fertile ovum editing information) and the fertile ovum evaluation information, displayed on the second terminal 40.

The second terminal 40 into which the acquisition request is input from the fertile ovum transplanter, transmits the acquisition request to the acquisition unit 24 through the network N. Next, the output unit 26 receives the fact that the acquisition unit 24 acquires the acquisition request from the second terminal 40, and transmits the assignment command according to the acquisition request to the first terminal 30 through the network N.

Next, the fertile ovum quality evaluator receives the fact that the first terminal 30 receives the assignment command from the output unit 26, and transmits the assignment command to the gateway terminal 10a through the network N. Then, the gateway terminal 10a receiving the assignment command from the first terminal 30, outputs the assignment command to the control recording PC 205.

The control recording PC 205 into which the assignment command is input, displays the information according to the assignment command, through the display device 206. Accordingly, the assignment command according to the acquisition request of the fertile ovum transplanter is notified to the fertile ovum manager managing the fertile ovum F. Then, the fertile ovum manager to which the assignment command is notified, performs the shipping and delivery of the fertile ovum F selected by the fertile ovum transplanter, on the basis of the acquisition request of the fertile ovum transplanter.

(Step S46: Progress Information Acquisition)

The fertile ovum transplanter transplants the fertile ovum F which is shipped and delivered from the fertile ovum manager, to the livestock, and performs the parturition and the propagation. Then, the immatures generated from the livestock are grown to the imago, and the imago is sold in the market. The fertile ovum transplanter obtains the progress information relevant to the fertile ovum F selected by himself, on the basis of the evaluation support information (the third fertile ovum analysis information, the identification information, the gene analysis information, and the gene editing information) and the fertile ovum evaluation information, while the fertile ovum F assigned from the fertile ovum manager is grown to the imago to be sold.

Next, the fertile ovum transplanter inputs the progress information obtained as described above, into the second terminal 40. Accordingly, the progress information relevant to the fertile ovum F selected by the fertile ovum transplanter from the second terminal 40, is transmitted to the acquisition unit 24 through the network N.

Then, the acquisition unit 24 acquiring the progress information, outputs the progress information to the analysis unit 25, the output unit 26, and the storage unit 28. The output unit 26 acquiring the progress information from the acquisition unit 24, transmits the progress information to the fertile ovum quality evaluator (the first terminal 30). In addition, the progress information output to the storage unit 28, is stored in the storage unit 28.

Here, the acquisition unit 24 of this embodiment acquires at least one of the transplant information, the propagation information, the fattening information, and the meat information, relevant to the fertile ovum F selected on the basis of the evaluation support information (the third fertile ovum analysis information, the identification information, the gene analysis information, and the gene editing information) and the fertile ovum evaluation information, as the progress information.

Subsequently, the analysis unit 25 acquiring the progress information from the acquisition unit 24, reads out at least one of the shape information, the motion information, the compaction information, the contraction information, the expansion information, the dormant information, the growing information according to findings, the quality information, the gene analysis information, the gene editing information, and the culture environment information, relevant to the fertile ovum F associated with the progress information, which are stored in the storage unit 28, from the storage unit 28.

Next, the analysis unit 25 installs the progress information and the information read out from the storage unit 28 in the algorithm set in advance, as the learning data, and thus, builds out again the identifier. Accordingly, the identifier is updated.

On the other hand, the progress information is displayed on the first terminal 30 acquiring the progress information from the acquisition unit 24. That is, the progress information relevant to the fertile ovum F selected on the basis of the evaluation support information (the third fertile ovum analysis information, the identification information, the gene analysis information, and the gene editing information) and the fertile ovum evaluation information, is notified to the fertile ovum quality evaluator. Accordingly, when the fertile ovum quality evaluator evaluates the quality of the fertile ovum F on the basis of the evaluation support information (the fertile ovum analysis report), it is possible to perform the quality evaluation also considering the progress information.

<Operation>

In the fertile ovum quality evaluation system 700 according to this embodiment, the acquisition request based on the evaluation support information (the third fertile ovum analysis information, the identification information, the gene analysis information, and the gene editing information) and the fertile ovum evaluation information, is input into the second terminal 40 by the fertile ovum transplanter.

Accordingly, the fertile ovum transplanter is capable of selecting and obtaining the fertile ovum F having desired quality, with reference to an analysis result of the second time-lapse image G2, the gene analysis information relevant to the fertile ovum F associated with the second time-lapse image G2, and the gene editing information, which are analyzed with a high degree of accuracy by the specialized AI, the evaluation information of the analysis result further evaluated by the fertile ovum quality evaluator, and the identification information relevant to the fertile ovum F.

Fifth Embodiment

Figure 20:
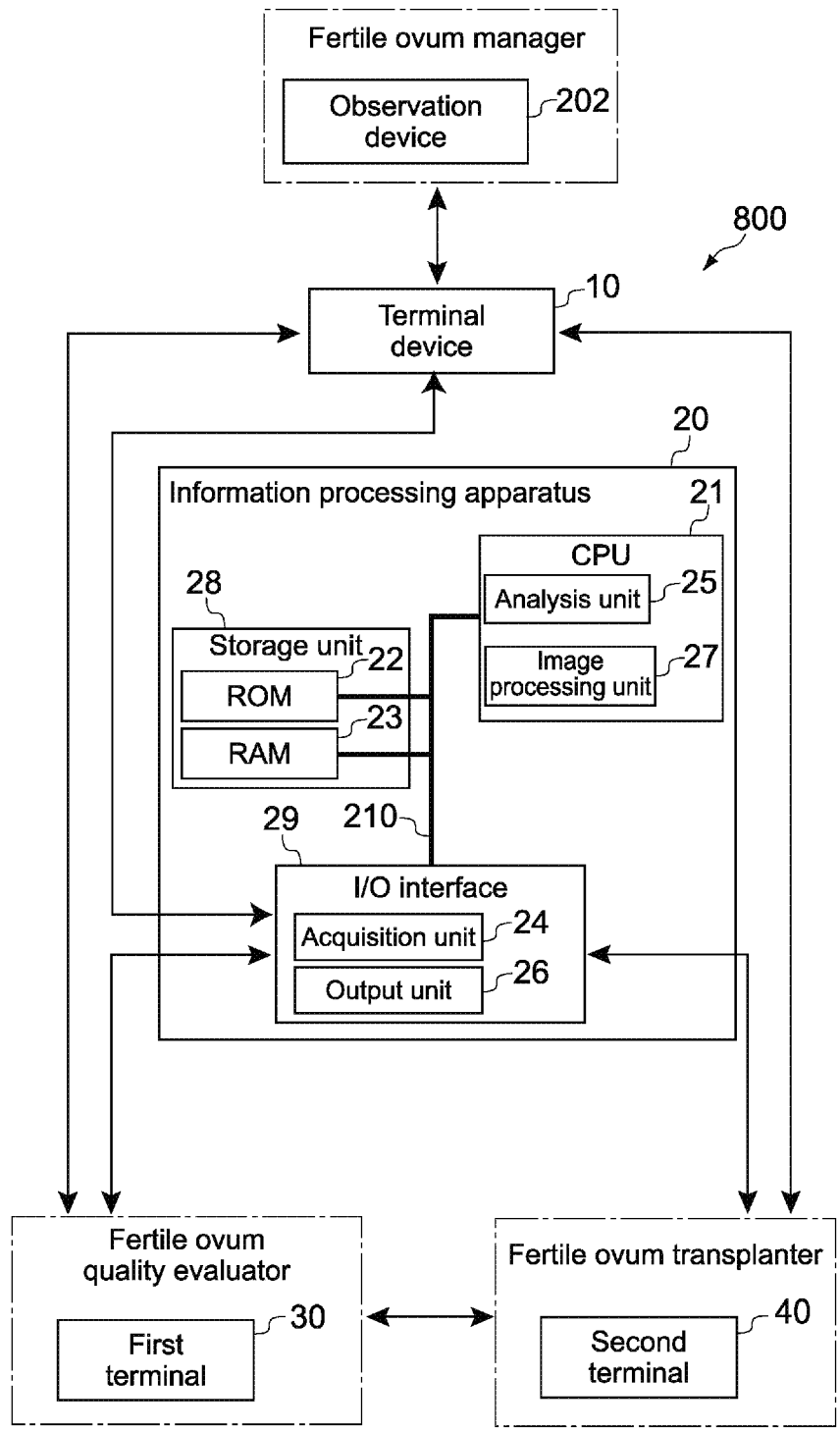
FIG. 20 is a block diagram of a fertile ovum quality evaluation system according to a fifth embodiment of the present technology.
Figure 21:
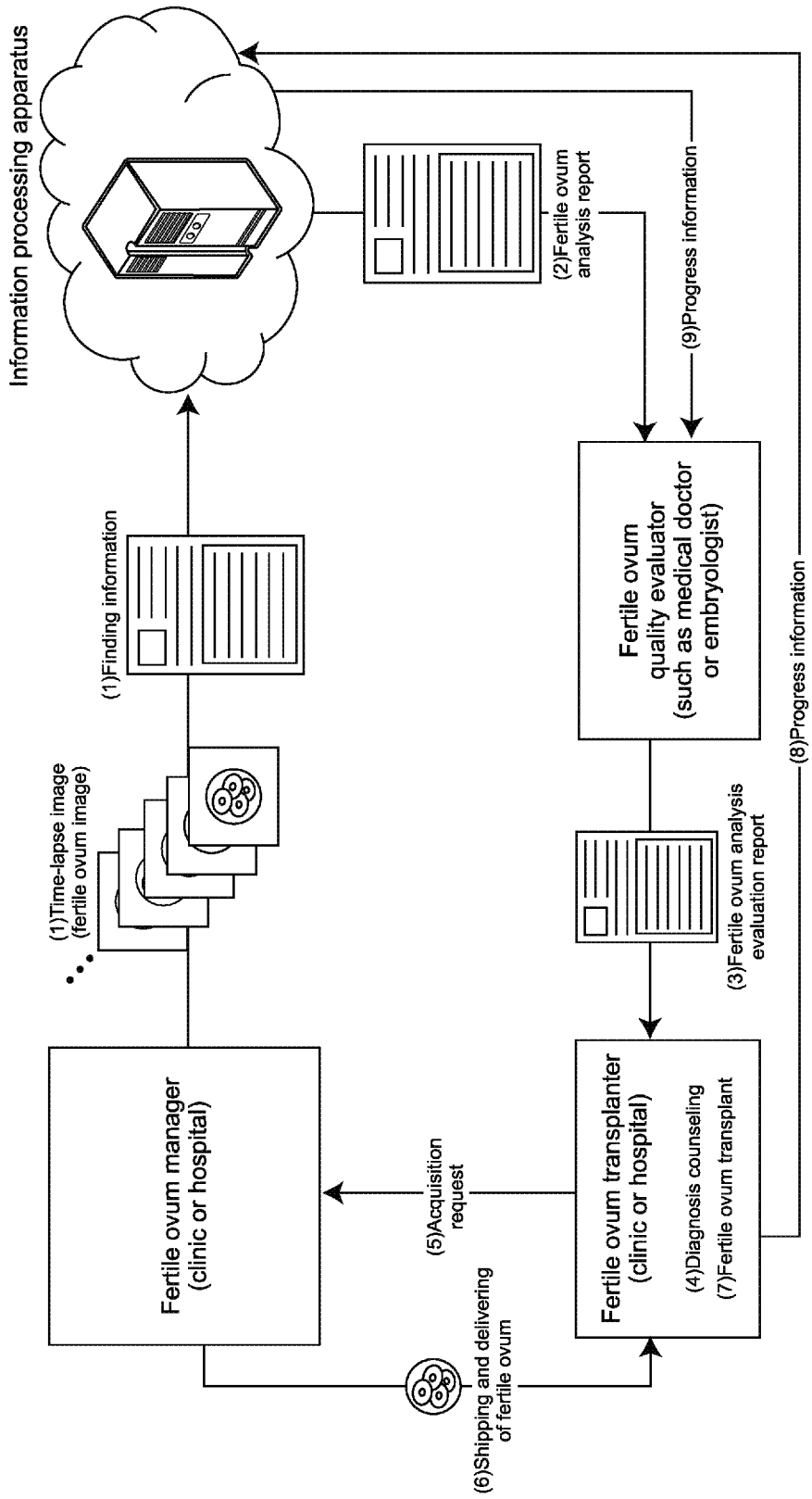
FIG. 21 is a diagram illustrating the outline of fertile ovum analysis support of the fertile ovum quality evaluation system.

FIG. 20 is a block diagram of a fertile ovum quality evaluation system 800 according to a fifth embodiment of the present technology. FIG. 21 is a diagram illustrating the outline of the fertile ovum analysis support of the fertile ovum quality evaluation system 800, and is a diagram illustrating a flow of analyzing the quality of the fertile ovum F, and of obtaining the progress information relevant to the fertile ovum. Hereinafter, the same reference numerals will be applied to the same constituents as those of the first embodiment, and the detailed description thereof will be omitted.

The fertile ovum quality evaluation system 800 according to this embodiment is a network system which is capable of mutually acquiring quality evaluation information of a human fertile ovum analyzed with a high degree of accuracy in a human reproductive clinic or a hospital culturing?managing the human fertile ovum (the fertile ovum manager), a medical doctor, an embryologist, or a staff belonging to the human reproductive clinic or the hospital (the fertile ovum quality evaluator), a human reproductive clinic or a hospital transplanting the human fertile ovum of which the quality is evaluated for a fertilization treatment (the fertile ovum transplanter), through the network such as the internet. Hereinafter, the quality evaluation method of the fertile ovum using the human fertile ovum as a target, will be described.

<Fertile Ovum Quality Evaluation Method>

Figure 22:
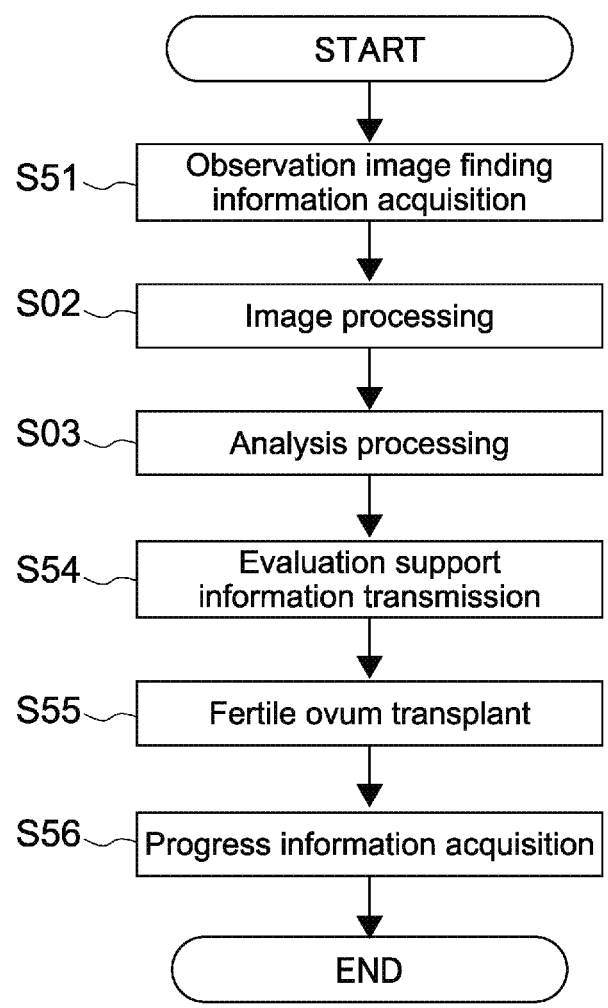
FIG. 22 is a flowchart illustrating a method of evaluating quality of a fertile ovum of the fertile ovum quality evaluation system.

FIG. 22 is a flowchart illustrating a method of evaluating the quality of the fertile ovum F of the fertile ovum quality evaluation system 800 according to this embodiment. Hereinafter, the quality evaluation method of the fertile ovum F will be described while suitably referring to FIG. 22. Note that the description of the same steps as those of the first embodiment will be omitted.

(Step S51: Observation Image?Finding Information Acquisition)

First, the fertile ovum quality evaluator inputs finding information relevant to the fertile ovum F, to the control recording PC 205 through the input unit 207. The finding information input into the control recording PC 205, is stored in the control recording PC 205, and is transmitted to the gateway terminal 10*a*. The gateway terminal 10*a* receiving the finding information, transmits the finding information to the acquisition unit 24 through the network N, and the acquisition unit 24 acquires the information.

Here, the finding information of this embodiment, for example, is information relevant to the quality of the fertile ovum F (the growing condition, the number of cells, the cell symmetry, the number of pronuclei, the number of polocytes, the number of nuclei in the cell blastomere, the fragment, or the like), which is determined by the expert such as the medical doctor or the embryologist, according to the findings, on the basis of the time-lapse images of the fertile ova F captured in chronological order.

Subsequently, the output unit 26 receives the fact that the acquisition unit 24 acquires the finding information from the gateway terminal 10*a* through the network N, and transmits the capturing command of capturing the fertile ovum F, to the gateway terminal 10*a* through the network N. The gateway terminal 10*a* receiving the capturing command, transmits the capturing command to the control recording PC 205.

The control recording PC 205 receiving the capturing command, controls the capturing unit 2021 according to the capturing command. Accordingly, as described in the first embodiment, the first time-lapse image G1 including six fertile ova F is generated, and the first time-lapse image G1 is transmitted to the control recording PC 205.

The control recording PC 205 into which the first time-lapse image G1 is input, transmits the first time-lapse image G1 to the gateway terminal 10*a*. The gateway terminal 10*a* receiving the first time-lapse image G1, transmits the first time-lapse image G1 to the acquisition unit 24 through the network N, and the acquisition unit 24 acquires the information.

The acquisition unit 24 outputs the first time-lapse image G1 and the finding information, acquired from the gateway terminal 10*a*, to the storage unit 28 through the network N, and the information is stored in the storage unit 28. In addition, the acquisition unit 24 outputs the acquired first time-lapse image G1 to the image processing unit 27, and outputs the finding information to the output unit 26.

(Step S54: Evaluation Support Information Transmission)

The output unit 26 generates the evaluation support information including at least the finding information acquired from the acquisition unit 24, and the first fertile ovum analysis information acquired from the analysis unit 25. Then, the output unit 26 outputs the evaluation support information to the fertile ovum quality evaluator through the network N.

The evaluation support information, for example, is transmitted to the first terminal 30, as "Fertile Ovum Analysis Report" for a fertile ovum quality evaluator. "Fertile Ovum Analysis Report", for example, may be displayed on the first terminal 30 through application software for a fertile ovum quality evaluator, which is installed in the first terminal 30.

The first terminal 30 receiving the evaluation support information, for example, displays the evaluation support information on the web browser, as the WEB dashboard. Accordingly, the quality evaluation of the fertile ovum F is supported by the fertile ovum quality evaluator. Specifically, the fertile ovum evaluation information based on the evaluation support information is input into the first terminal 30 by the fertile ovum quality evaluator evaluating?brow sing the evaluation support information displayed on the first terminal 30.

Note that the fertile ovum quality evaluation system 800 according to this embodiment is a network system which preserves "Guideline relevant to Safety Management of Medical Information System" (so-called 3-province-4-guideline). Accordingly, the action of the fertile ovum quality evaluator of inputting the fertile ovum evaluation information into the first terminal 30, on the basis of the evaluation support information, does not correspond to "Diagnostic Action" of examining patients.

(Step S55: Fertile Ovum Transplant)

The first terminal 30 transmits the evaluation support information acquired from the output unit 26 (the first fertile ovum analysis information and the finding information), and the fertile ovum evaluation information input by the fertile ovum quality evaluator, to the second terminal 40 through the network N.

Such information transmitted to the second terminal 40, for example, is transmitted to the second terminal 40, as "Fertile Ovum Analysis?Evaluation Report" provided for the fertile ovum transplanter. "Fertile Ovum Analysis?Evaluation Report", for example, may be displayed on the second terminal 40 through application software for a fertile ovum transplanter, which is installed in the second terminal 40.

The second terminal 40 acquiring the evaluation support information (the first fertile ovum analysis information and the finding information) and the fertile ovum evaluation information, for example, displays the information on the web browser, as the WEB dashboard. Accordingly, for example, a fertile ovum analysis?evaluation report is reported to an infertile patient visiting the fertile ovum transplanter (the human reproductive clinic, the hospital, or the like), and thus, it is useful for planning and managing diagnosis reservation or hospital visit management of the infertile patient, and hospital visit schedule or medication schedule of the infertile patient.

Subsequently, the medical doctor or the like, belonging to the fertile ovum transplanter, performs diagnosis?counseling in order to transplant the fertile ovum F to the infertile patient, with reference to the evaluation support information (the first fertile ovum analysis information and the finding information) and the fertile ovum evaluation information, displayed on the second terminal 40. At this time, for example, the fertile ovum F having desired quality of the infertile patient is selected from the plurality of fertile ova F generated by external fertilization between an ovum of the infertile patient and a sperm of a partner, or an ovum of the partner and a sperm of the infertile patient, which are managed by the fertile ovum manager, with reference to the fertile ovum analysis?evaluation report (the evaluation support information and the fertile ovum evaluation information).

Next, the medical doctor or the like belonging to the fertile ovum transplanter, inputs the acquisition request of acquiring the fertile ovum F which is selected as a result of the diagnosis?counseling with respect to the infertile patient, into the second terminal 40. The second terminal 40 into which the acquisition request is input, transmits the acquisition request to the gateway terminal 10*a* through the network N. Then, the gateway terminal 10a receiving the acquisition request from the second terminal 40, outputs the acquisition request to the control recording PC 205.

The control recording PC 205 into which the acquisition request is input, displays the information according to the acquisition request, through the display device 206. Accordingly, the acquisition request of the fertile ovum transplanter is notified to the fertile ovum manager managing the fertile ovum F. Then, the fertile ovum manager to which the acquisition request is notified, performs shipping?delivery of the fertile ovum F selected by the fertile ovum transplanter, on the basis of the acquisition request of the fertile ovum transplanter.

Next, the fertile ovum transplanter receives the fertile ovum F selected as a result of the diagnosis?counseling based on the fertile ovum analysis?evaluation report, from the fertile ovum manager, and transplants the fertile ovum F to the uterus of the infertile patient.

(Step S56: Progress Information Acquisition)

The fertile ovum transplanter obtains the progress information relevant to the fertile ovum F selected on the basis of the fertile ovum analysis?evaluation report (the evaluation support information and the fertile ovum evaluation information), while the fertile ovum F transplanted to the uterus of the infertile patient, is grown to be subjected to parturition.

Next, the medical doctor or the like belonging to the fertile ovum transplanter, inputs the progress information obtained as described above, into the second terminal 40. Accordingly, the progress information relevant to the fertile ovum F selected by the fertile ovum transplanter from the second terminal 40, is transmitted to the acquisition unit 24 through the network N.

Then, the acquisition unit 24 acquiring the progress information, outputs the progress information to the analysis unit 25, the output unit 26, and the storage unit 28. The output unit 26 acquiring the progress information from the acquisition unit 24, transmits the progress information to the fertile ovum quality evaluator (the first terminal 30). In addition, the progress information output to the storage unit 28, is stored in the storage unit 28.

Here, the acquisition unit 24 of this embodiment, acquires at least the transplant information relevant to the fertile ovum F selected on the basis of the evaluation support information (the first fertile ovum analysis information and the finding information) and the fertile ovum evaluation information, as the progress information.

Subsequently, the analysis unit 25 acquiring the progress information from the acquisition unit 24, reads out at least one of the shape information, the motion information, the compaction information, the contraction information, the expansion information, the dormant information, the growing information according to findings, the quality information, the gene analysis information, and the culture environment information, relevant to the fertile ovum F associated with the progress information, which are stored in the storage unit 28, from the storage unit 28.

Next, the analysis unit 25 installs the progress information, and the information read out from the storage unit 28, in the algorithm set in advance, as the learning data, and thus, builds out again the identifier. Accordingly, the identifier is updated.

On the other hand, the progress information is displayed on the first terminal 30 acquiring the progress information from the acquisition unit 24. That is, the progress information relevant to the fertile ovum F selected on the basis of the evaluation support information (the first fertile ovum analysis information and the finding information) and the fertile ovum evaluation information, is notified to the fertile ovum quality evaluator. Accordingly, when the fertile ovum quality evaluator evaluates the quality of the fertile ovum F on the basis of the evaluation support information (the fertile ovum analysis report), it is possible to perform the quality evaluation also considering the progress information.

<Operation>

In the fertile ovum quality evaluation system 800 of this embodiment, it is possible to select the fertile ovum F having desired quality of the infertile patient, with reference to an analysis result of the second time-lapse image G2 analyzed with a high degree of accuracy by the specialized AI, the evaluation information of the analysis result further evaluated by the fertile ovum quality evaluator, and the finding information relevant to the fertile ovum F associated with the second time-lapse image G2, and to transplant the fertile ovum F to the infertile patient.

<Complement>

Figure 23:
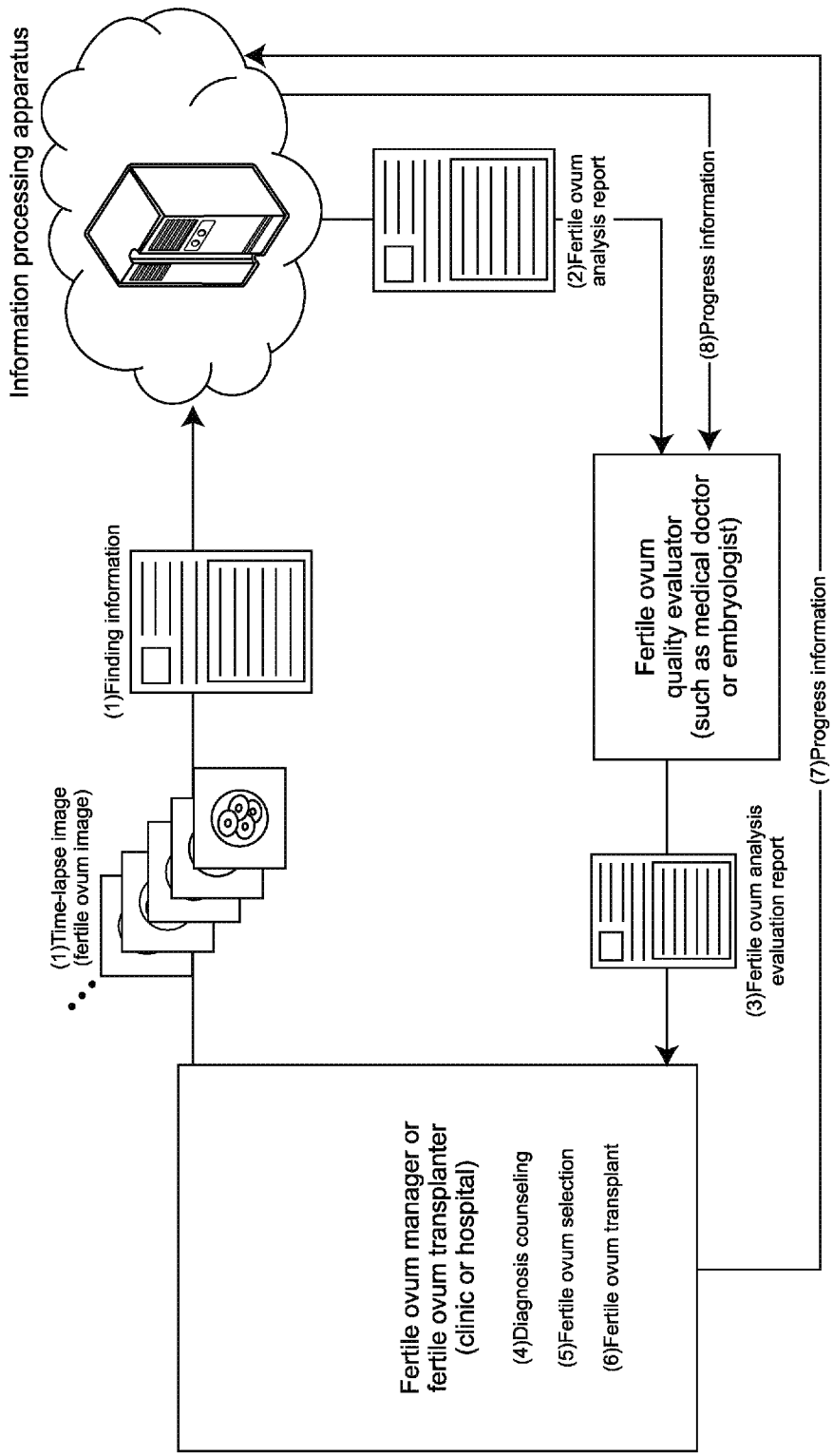
FIG. 23 is a diagram illustrating the other outline of the fertile ovum analysis support of the fertile ovum quality evaluation system.

FIG. 23 is a diagram illustrating the other outline of the fertile ovum analysis support of the fertile ovum quality evaluation system 800, and is a diagram illustrating a flow of analyzing the quality of the fertile ovum F, and of obtaining the progress information relevant to the fertile ovum.

As illustrated in FIG. 23, in the fertile ovum quality evaluation system 800 of this embodiment, the fertile ovum quality evaluator evaluating the quality of the fertile ovum F and the fertile ovum transplanter transplanting the fertile ovum F may be the same institution (the hospital, the human reproductive clinic, or the like). That is, in the fertile ovum quality evaluation system 800, the management of the fertile ovum F and the transplant of the fertile ovum F with respect to the infertile patient may be performed in the same institution (the hospital, the human reproductive clinic, or the like). Accordingly, a step of shipping?delivering the fertile ovum F with respect to the fertile ovum transplanter is omitted, and thus, it is possible to promptly transplant the fertile ovum F to the infertile patient.

Modification Example

In Step S51 of the fertile ovum quality evaluation system 800 of this embodiment, the finding information is input into the control recording PC 205 through the input unit 207, but the present technology is not limited thereto, and the identification information described in the first embodiment may be further input. That is, the evaluation support information including at least the first fertile ovum analysis information, the fertile ovum evaluation information, the finding information, and the identification information, may be presented to the fertile ovum transplanter or the patient through the second terminal 40.

As described above, the embodiments of the present technology have been described, but the present technology is not limited to the embodiments described above, and it is obvious that various changes can be added.

For example, in the fertile ovum quality evaluation systems 100, 300, 500, 700, and 800, a capturing step of capturing the fertile ovum F is repeated at an arbitrary time, for example, at 15-minute intervals or at each predetermined period such as every other day, or continuously, and the quality of the fertile ovum F is evaluated by using an image acquired by the step, but the present technology is not limited thereto.

In the fertile ovum quality evaluation systems 100, 300, 500, 700, and 800 according to this embodiment, the image may be acquired in real time, as necessary, or the image of the fertile ovum F may be displayed on the display device 206 or the first and second terminals 30 and 40 to be observed and evaluated at any time.

In addition, in the first embodiment, the third embodiment, and the fourth embodiment described above, the output unit 26 receives the fact that the acquisition unit 24 acquires the acquisition request (the purchase request) from the fertile ovum transplanter, and transmits the assignment command (the sales command) according to the acquisition request (the purchase request) to the first terminal 30, but is not limited thereto.

For example, the output unit 26 may receives the fact that the acquisition unit 24 acquires the acquisition request (the purchase request) from the second terminal 40, and may output the assignment command (the sales command) according to the acquisition request (the purchase request), to the fertile ovum manager through the terminal device 10, and thus, the shipping and delivery of the fertile ovum F may be executed.

Further, in the first embodiment, the third embodiment, and the fourth embodiment described above, the acquisition request (the purchase request) input into the second terminal 40, is output to the information processing apparatus 20, but is not limited thereto, and the acquisition request (the purchase request) may be directly output to the fertile ovum manager through the terminal device 10, and thus, the shipping and delivery of the fertile ovum F may be executed.

In addition, in the fertile ovum quality evaluation systems 100, 300, 500, and 700 according to the present technology, the fertile ovum F, which is a target, is typically derived from the cattle, but is not limited thereto, and for example, may be sampled from mice, pigs, dogs, cats, or the like.

In addition, herein, "Fertile Ovum" conceptually includes at least a single cell, and an aggregate of a plurality of cells. In addition, the single sell or the aggregate of the plurality of cells, relate to a cell observed in one or a plurality of stages of embryo development (fertile ovumnic development), including an egg mother cell (an oocyte), an ovum (egg/ovum), a fertile ovum (fertile ovum/zygote), a blastodermic vesicle (a blastocyst), and an embryo (a fertile ovum).

Further, the present technology can also be applied to an arbitrary cell such as an unfertilized egg cell (ovum) or embryo of a living object in the field of animal industry or the like, or a biological sample taken out from the living object, such as a stem cell, an immune cell, and a cancer cell in the field of regenerative medicine, pathological biology, a gene editing technology, or the like.

Further, the present technology may be implemented in any of numerous system architectures. For instance, in one embodiment, the system may include at least one server configured to process a time-series of images received from imager. In another embodiment, the system may include an imaging device comprising a communications interface configured to connect via at least one network to at least one computer from which a computer program is downloaded to the imaging device or another computer. The downloaded computer program may be used to control operations of the imaging device (e.g., capturing of images) and/or perform image processing in accordance with the techniques described herein.

Note that the present technology can also be configured as follows.

(1)

A computer system for evaluating the quality of a fertile ovum, the computer system including:
  computer processing circuitry configured to:
    receive a plurality of images of a fertile ovum captured in time-series by an imaging apparatus;
    provide as input to at least one learned model, the plurality of images of the fertile ovum or information based on the plurality of images of the fertile ovum, wherein the at least one learned model has been trained to output, based at least in part, on the plurality of images, fertile ovum analysis information describing characteristics of the fertile ovum used to evaluate a quality of fertile ovum; and
    provide, on a web dashboard provided in a web browser, evaluation support information based, at least in part, on the fertile ovum analysis information, wherein the evaluation support information enables a quality evaluator to interact with the web dashboard to modify at least some of the evaluation support information.

(2)

The computer system of (1), wherein the computer processing circuitry is further configured to process the plurality of images received from the imaging apparatus to generate the information based on the plurality of images provided as input to the at least one learned model.

(3)

The computer system of (2), wherein processing the plurality of images includes performing normalization processing on the plurality of images.

(4)

The computer system of (2), wherein processing the plurality of images includes defining, within each of the plurality of images, a boundary of the fertile ovum.

(5)

The computer system of (2), wherein processing the plurality of images includes performing deep learning analysis to extract a profile line of the fertile ovum in the plurality of images.

(6)

The computer system of (1), wherein the computer processing circuitry is further configured to train the at least one learned model based, at least in part on, one or more of shape information, compaction information, contraction information, expansion information, dormant information, and quality information.

(7)

The computer system of (6), wherein the quality information includes information describing a growing condition of the fertile ovum (8)

The computer system of (6), wherein the shape information includes information describing a change in one or more of a diameter, an area, a volume, and a roundness of the fertile ovum.

(9)

The computer system of (6), wherein the compaction information includes information describing a compaction time when a shape of the fertile ovum is changed from a 16-cell stage to a morula stage.

(10)

The computer system of (6), wherein the contraction information includes information describing one or more of a number of contractions, a contraction diameter, a contraction speed, a contraction time, a contraction interval, a contraction strength, and a contraction frequency of the fertile ovum.

(11)

The computer system of (6), wherein the dormant information includes information describing a lag-phase during development of the fertile ovum.

(12)

The computer system of (1), wherein the computer processing circuitry is further configured to:
receive, via the web dashboard, input from the quality evaluator as fertile ovum evaluation information; and
provide, via the web dashboard, access to at least some of the evaluation support information and the fertile ovum evaluation information to a fertile ovum consumer.

(13)

The computer system of (12), wherein the computer processing circuitry is further configured to:
receive, via the web dashboard, an acquisition request for a fertile ovum from the fertile ovum consumer; and
initiate a transfer process for transferring the requested fertile ovum to the fertile ovum consumer in response to receiving the acquisition request.

(14)

The computer system of claim (1), wherein the computer processing circuitry is further configured to:
receive, via the web dashboard, progress information including information describing a condition of an animal from which the fertile ovum was grown; and
retraining the learned model based, at least in part, on the progress information.

(15)

The computer system of (1), further including:
the imaging apparatus configured to capture the plurality of images of the fertile ovum in time series.

(16)

A computer-implemented method for analyzing time series images of a fertile ovum, the method including:
receiving, from an imaging apparatus, a plurality of images of a fertile ovum captured in time-series;
providing as input to at least one learned model, the plurality of images of the fertile ovum or information based on the plurality of images, wherein the at least one learned model has been trained to output, based at least in part, on the plurality of images, fertile ovum analysis information describing characteristics of the fertile ovum used to evaluate a quality of fertile ovum; and
displaying, on a web dashboard provided in a web browser, evaluation support information based, at least in part, on the fertile ovum analysis information, wherein the evaluation support information enables a quality evaluator to interact with the web dashboard to modify at least some of the evaluation support information.

(17)

The computer-implemented method of (16), further including:
processing the plurality of images received from the imaging apparatus to generate the information based on the plurality of images provided as input to the at least one learned model.

(18)

The computer-implemented method of (16), further including:
training the at least one learned model based, at least in part on, one or more of shape information, compaction information, contraction information, expansion information, dormant information, and quality information.

(19)

The computer-implemented method of (16), further including:
receiving, via the web dashboard, input from the quality evaluator as fertile ovum evaluation information; and
providing, via the web dashboard, access to at least some of the evaluation support information and the fertile ovum evaluation information to a fertile ovum consumer.

(20)

The computer-implemented method of (19), further including:
receiving, via the web dashboard, an acquisition request for a fertile ovum from the fertile ovum consumer; and
initiating a transfer process for transferring the requested fertile ovum to the fertile ovum consumer in response to receiving the acquisition request.

(21)

The computer-implemented method of (16), further including:
receiving, via the web dashboard, progress information including information describing a condition of an animal from which the fertile ovum was grown; and
retraining the learned model based, at least in part, on the progress information.

(22)

A non-transitory computer readable medium encoded with a plurality of instructions that, when executed by computer processing circuitry, perform a method including:
receiving, from an imaging apparatus, a plurality of images of a fertile ovum captured in time-series;
providing as input to at least one learned model, the plurality of images of the fertile ovum or information based on the plurality of images, wherein the at least one learned model has been trained to output, based at least in part, on the plurality of images, fertile ovum analysis information describing characteristics of the fertile ovum used to evaluate a quality of fertile ovum; and
displaying, on a web dashboard provided in a web browser, evaluation support information based, at least in part, on the fertile ovum analysis information, wherein the evaluation support information enables a quality evaluator to interact with the web dashboard to modify at least some of the evaluation support information.

(23)

A computer system for evaluating the quality of a fertile ovum, the computer system including:
computer processing circuitry configured to:
receive a plurality of images of a fertile ovum captured in time-series by an imaging apparatus;
provide as input to at least one learned model, the plurality of images of the fertile ovum or information based on the plurality of images of the fertile ovum, wherein the at least one learned model has been trained to output, based at least in part, on the plurality of images, fertile ovum analysis information describing characteristics of the fertile ovum used to evaluate a quality of fertile ovum; and
provide, on a web dashboard provided in a web browser, evaluation support information based, at least in part, on the fertile ovum analysis information, wherein the evaluation support information enables a quality evaluator to interact with the web dashboard to input quality information of the fertile ovum.

(24)

An imaging processing system for evaluating the quality of a fertile ovum, the image processing system including:
an imaging device configured to capture a time-series of images of a fertile ovum, wherein at least a part of the images in the time-series correspond to different developmental stages of the fertile ovum;
a communications interface configured to connect via at least one network to at least one computer; and
at least one storage medium configured to store a plurality of instructions received via the communications interface, wherein the plurality of instructions, when executed by computer processing circuitry, cause the computer processing circuitry to:
control capturing of the time-series of images by the imaging device; provide the time-series of images or information based on the time-series of images to at least one learned model, wherein the at least one learned model has been trained to output, based at least in part, on the time-series of images, fertile ovum analysis information describing characteristics of the fertile ovum used to evaluate a quality of fertile ovum; and
provide, on a web dashboard provided in a web browser, evaluation support information based, at least in part, on the fertile ovum analysis information, wherein the evaluation support information enables a quality evaluator to interact with the web dashboard to input quality information of the fertile ovum.

(25)

An imaging processing system for evaluating the quality of a fertile ovum, the image processing system including:
an imaging device configured to capture a time-series of images of a fertile ovum, wherein at least a part of the images in the time-series correspond to different developmental stages of the fertile ovum;
a communications interface configured to connect via at least one network to at least one computer; and
at least one storage medium configured to store a plurality of instructions received via the communications interface, wherein the plurality of instructions, when executed by computer processing circuitry, cause the computer processing circuitry to:
provide the time-series of images or information based on the time-series of images to at least one learned model, wherein the at least one learned model has been trained to output, based at least in part, on the time-series of images, fertile ovum analysis information describing characteristics of the fertile ovum used to evaluate a quality of fertile ovum; and
provide, on a web dashboard provided in a web browser, evaluation support information based, at least in part, on the fertile ovum analysis information, wherein the evaluation support information enables a quality evaluator to interact with the web dashboard to input quality information of the fertile ovum.

(26)

An imaging processing system for evaluating the quality of a fertile ovum, the image processing system including:
at least one storage medium configured to store a plurality of instructions that, when executed by computer processing circuitry, cause the computer processing circuitry to:
provide a time-series of images captured by an imaging device or information based on the time-series of images to at least one learned model, wherein the at least one learned model has been trained to output, based at least in part, on the time-series of images, fertile ovum analysis information describing characteristics of the fertile ovum used to evaluate a quality of fertile ovum; and
provide, on a web dashboard provided in a web browser, evaluation support information based, at least in part, on the fertile ovum analysis information, wherein the evaluation support information enables a quality evaluator to interact with the web dashboard to input quality information of the fertile ovum.

(27)

A fertile ovum quality evaluation method, including:
acquiring a time-lapse image of a fertile ovum from a production operator through a network;
generating first fertile ovum analysis information by applying the time-lapse image of the fertile ovum to a learned model which is generated by using time-lapse images of fertile ova collected from a plurality of production operators; and
outputting a fertile ovum analysis report to an embryologist or a farm producer that evaluates the fertile ovum by using the fertile ovum analysis report including the first fertile ovum analysis information, through the network.

(28)

The fertile ovum quality evaluation method according to (27) described above, in which
the step of generating the first fertile ovum analysis information includes generating the first fertile ovum analysis information by performing deep learning analysis with respect to the time-lapse image of the fertile ovum in accordance with the learned model.

(29)

The fertile ovum quality evaluation method according to (27) or (28) described above, further including:
transmitting a fertile ovum sales report to a breeder.

(30)

The fertile ovum quality evaluation method according to any one of (27) to (29) described above, in which
the step of outputting the fertile ovum analysis report includes outputting the fertile ovum analysis report including at least one of a capturing time for capturing the fertile ovum, a growing time of the fertile ovum, quality information, shape information, motion information, compaction information, contraction information, expansion information, and dormant information, as the first fertile ovum analysis information.

(31)

The fertile ovum quality evaluation method according to any one of (27) to (30) described above, in which
the step of generating the first fertile ovum analysis information includes generating the first fertile ovum analysis information by applying the time-lapse image of the fertile ovum to a first identifier generated on a basis of a first algorithm that sets the time-lapse images of the fertile ova collected from the plurality of production operators as learning data.

(32)

The fertile ovum quality evaluation method according to (31) described above, further including:
normalizing the time-lapse image of the fertile ovum before the first fertile ovum analysis information is generated, in which
the step of generating the first fertile ovum analysis information includes generating the first fertile ovum analysis information by applying the normalized time-lapse image of the fertile ovum to the first identifier.

(33)

The fertile ovum quality evaluation method according to (31) or (32) described above, in which the step of generating the first fertile ovum analysis information includes generating the first fertile ovum analysis information by applying the time-lapse image of the fertile ovum to a second identifier generated on a basis of a second algorithm that sets the time-lapse images of the fertile ova collected from the plurality of production operators as learning data and the first algorithm.

(34)

The fertile ovum quality evaluation method according to any one of (27) to (33) described above, in which
the step of generating the first fertile ovum analysis information includes generating the first fertile ovum analysis information by applying the time-lapse image of the fertile ovum and identification information to an identifier generated on a basis of an algorithm that sets the time-lapse images of the fertile ova collected from the plurality of production operators and the identification information as learning data.

(35)

The fertile ovum quality evaluation method according to any one of (27) to (34) described above, in which
the step of generating the first fertile ovum analysis information includes generating the first fertile ovum analysis information by applying the time-lapse image of the fertile ovum and culture environment information to an identifier generated on a basis of an algorithm that sets the time-lapse images of the fertile ova collected from the plurality of production operators and the culture environment information as learning data.

(36)

The fertile ovum quality evaluation method according to any one of (27) to (35) described above, in which
the step of generating the first fertile ovum analysis information includes generating at least one of a capturing time for capturing the fertile ovum, a growing time of the fertile ovum, quality information, shape information, motion information, compaction information, contraction information, expansion information, and dormant information, as the first fertile ovum analysis information.

(37)

The fertile ovum quality evaluation method according to any one of (29) to (36) described above, in which
the step of transmitting the fertile ovum sales report includes transmitting the fertile ovum sales report including evaluation support information which includes the first fertile ovum analysis information and supports quality evaluation of the fertile ovum, and fertile ovum evaluation information based on the evaluation support information, to the breeder.

(38)

The fertile ovum quality evaluation method according to any one of (29) to (37) described above, further including:
acquiring an acquisition request of acquiring the fertile ovum from the breeder through the network; and
outputting a command according to the acquisition request to the farm producer or the embryologist.

(39)

The fertile ovum quality evaluation method according to any one of (29) to (37) described above, further including:
acquiring a purchase request of purchasing the fertile ovum from the breeder through the network; and
outputting a command according to the purchase request to the farm producer or the embryologist.

(40)

The fertile ovum quality evaluation method according to (39) described above, further including:
determining whether or not to respond to the purchase request from the breeder.

(41)

The fertile ovum quality evaluation method according to any one of (29) to (40) described above, further including:
acquiring gene analysis information which is acquired by a gene analysis device that analyzes a gene of the fertile ovum, from the production operator through the network;
generating second fertile ovum analysis information on a basis of the time-lapse image of the fertile ovum and the gene analysis information; and
outputting the second fertile ovum analysis information to the embryologist or the farm producer through the network.

(42)

The fertile ovum quality evaluation method according to (41) described above, further including:
acquiring gene editing information which is acquired by a gene editing device that edits the gene of the fertile ovum, from the production operator through the network;
generating third fertile ovum analysis information on a basis of the time-lapse image of the fertile ovum, the gene analysis information, and the gene editing information; and
outputting the third fertile ovum analysis information to the embryologist or the farm producer through the network.

(43)

The fertile ovum quality evaluation method according to any one of (29) to (42) described above, further including:
acquiring progress information relevant to the fertile ovum from the breeder through the network; and
outputting the progress information to the farm producer or the embryologist through the network.

(44)

The fertile ovum quality evaluation method according to (43) described above, in which
the step of acquiring the progress information includes acquiring at least one of transplant information relevant to the fertile ovum, propagation information, fattening information, and meat information, as the progress information.

(45)

A fertile ovum quality evaluation system, including:
an information processing apparatus for performing quality evaluation of a fertile ovum according to cloud computing,
the information processing apparatus including
an acquisition unit that acquires a plurality of observation images in which fertile ova associated with intrinsic identification information are captured in chronological order, from a terminal device through a network,
an analysis unit that generates fertile ovum analysis information on a basis of the plurality of observation images, and
an output unit that outputs evaluation support information including the identification information and the fertile ovum analysis information to a computer that receives input of fertile ovum evaluation information based on the evaluation support information, through the network.

(46)

The fertile ovum quality evaluation system according to (45) described above, further including:
the terminal device configured to be capable of transmitting the plurality of observation images through the network.

(47)

The fertile ovum quality evaluation system according to (45) or (46) described above, in which
the acquisition unit further acquires at least one of information relevant to a sperm and an ovum which become the fertile ovum, mating information relevant to the fertile ovum, and information relevant to a culture dish for culturing the fertile ovum, as the identification information, from the terminal device through the network.

(48)

The fertile ovum quality evaluation system according to any one of (45) to (47) described above, in which
the information processing apparatus is a web server.

(49)

A fertile ovum quality evaluation system, including:
a cloud server capable of being connected to a plurality of terminals through a network,
the cloud server including
an acquisition unit that acquires a plurality of observation images in which fertile ova associated with intrinsic identification information are captured in chronological order, from a terminal device through the network;
an analysis unit that generates fertile ovum analysis information on a basis of the plurality of observation images, and
an output unit that outputs evaluation support information including the identification information and the fertile ovum analysis information to a computer that receives input of fertile ovum evaluation information based on the evaluation support information, through the network.

(50)

A program that causes an information processing apparatus to execute the steps of:
acquiring a time-lapse image of a fertile ovum from a production operator through a network;
generating fertile ovum analysis information by applying the time-lapse image of the fertile ovum to a learned model which is generated by using time-lapse images of fertile ova collected from a plurality of production operators; and
outputting a fertile ovum analysis report to an embryologist or a farm producer that evaluates the fertile ovum by using the fertile ovum analysis report including the fertile ovum analysis information, through the network.

(51)

An information processing apparatus, including:
an acquisition unit that acquires a time-lapse image of a fertile ovum from a production operator through a network;
an analysis unit that generates fertile ovum analysis information by applying the time-lapse image of the fertile ovum to a learned model which is generated by using time-lapse images of fertile ova collected from a plurality of production operators; and
an output unit that outputs a fertile ovum analysis report to an embryologist or a farm producer that evaluates the fertile ovum by using the fertile ovum analysis report including the fertile ovum analysis information, through the network.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

10 Terminal device
10a Gateway terminal
20 Information processing apparatus
24 Acquisition unit
25 Analysis unit
26 Output unit
27 Image processing unit
28 Storage unit
30 First terminal
40 Second terminal
202 Observation device
220 Determination unit
400 Gene analysis device
500 Gene editing device
100, 300, 500, 700, 800 Fertile ova quality evaluation system
F Fertile ovum

The invention claimed is:

1. A computer system for evaluating the quality of a fertile ovum, the computer system comprising:
computer processing circuitry configured to:
receive a plurality of images of a fertile ovum captured in time-series by an imaging apparatus;
process the plurality of images of the fertile ovum received from the imaging apparatus to generate information based on the plurality of images of the fertile ovum, wherein processing the plurality of images comprises performing deep learning analysis to extract a profile line of the fertile ovum in the plurality of images;
provide as input to at least one learned model, the plurality of images of the fertile ovum or the generated information based on the plurality of images of the fertile ovum, wherein the at least one learned model has been trained to output, based at least in part, on the plurality of images, fertile ovum analysis information describing characteristics of the fertile ovum used to evaluate a quality of fertile ovum; and
provide, on a web dashboard provided in a web browser, evaluation support information based, at least in part, on the fertile ovum analysis information, wherein the evaluation support information enables a quality evaluator to interact with the web dashboard to modify at least some of the evaluation support information.

2. The computer system of claim 1, wherein processing the plurality of images comprises performing normalization processing on the plurality of images.

3. The computer system of claim 1, wherein processing the plurality of images comprises defining, within each of the plurality of images, a boundary of the fertile ovum.

4. The computer system of claim 1, wherein the computer processing circuitry is further configured to train the at least one learned model based, at least in part on, one or more of shape information, compaction information, contraction information, expansion information, dormant information, and quality information.

5. The computer system of claim 4, wherein the quality information comprises information describing a growing condition of the fertile ovum.

6. The computer system of claim 4, wherein the shape information comprises information describing a change in one or more of a diameter, an area, a volume, and a roundness of the fertile ovum.

7. The computer system of claim 4, wherein the compaction information comprises information describing a compaction time when a shape of the fertile ovum is changed from a 16-cell stage to a morula stage.

8. The computer system of claim 4, wherein the contraction information comprises information describing one or more of a number of contractions, a contraction diameter, a contraction speed, a contraction time, a contraction interval, a contraction strength, and a contraction frequency of the fertile ovum.

9. The computer system of claim 4, wherein the dormant information comprises information describing a lag-phase during development of the fertile ovum.

10. The computer system of claim 1, wherein the computer processing circuitry is further configured to:
receive, via the web dashboard, progress information including information describing a condition of an animal from which the fertile ovum was grown; and
retrain the learned model based, at least in part, on the progress information.

11. The computer system of claim 1, further comprising:
the imaging apparatus configured to capture the plurality of images of the fertile ovum in time series.

12. A computer system for evaluating the quality of a fertile ovum, the computer system comprising:
computer processing circuitry configured to:
receive a plurality of images of a fertile ovum captured in time-series by an imaging apparatus;
provide as input to at least one learned model, the plurality of images of the fertile ovum or information based on the plurality of images of the fertile ovum, wherein the at least one learned model has been trained to output, based at least in part, on the plurality of images, fertile ovum analysis information describing characteristics of the fertile ovum used to evaluate a quality of fertile ovum;
provide, on a web dashboard provided in a web browser, evaluation support information based, at least in part, on the fertile ovum analysis information, wherein the evaluation support information enables a quality evaluator to interact with the web dashboard to modify at least some of the evaluation support information;
receive, via the web dashboard, input from the quality evaluator as fertile ovum evaluation information;
provide, via the web dashboard, access to at least some of the evaluation support information and the fertile ovum evaluation information to a fertile ovum consumer
receive, via the web dashboard, an acquisition request for a fertile ovum from the fertile ovum consumer; and
initiate a transfer process for transferring the requested fertile ovum to the fertile ovum consumer in response to receiving the acquisition request.

13. A computer-implemented method for analyzing time series images of a fertile ovum, the method comprising:
receiving, from an imaging apparatus, a plurality of images of a fertile ovum captured in time-series;
providing as input to at least one learned model, the plurality of images of the fertile ovum or information based on the plurality of images, wherein the at least one learned model has been trained to output, based at least in part, on the plurality of images, fertile ovum analysis information describing characteristics of the fertile ovum used to evaluate a quality of fertile ovum;
displaying, on a web dashboard provided in a web browser, evaluation support information based, at least in part, on the fertile ovum analysis information, wherein the evaluation support information enables a quality evaluator to interact with the web dashboard to modify at least some of the evaluation support information;
receiving, via the web dashboard, input from the quality evaluator as fertile ovum evaluation information;
providing, via the web dashboard, access to at least some of the evaluation support information and the fertile ovum evaluation information to a fertile ovum consumer;
receiving, via the web dashboard, an acquisition request for a fertile ovum from the fertile ovum consumer; and
initiating a transfer process for transferring the requested fertile ovum to the fertile ovum consumer in response to receiving the acquisition request.

14. The computer-implemented method of claim 13, further comprising:
processing the plurality of images received from the imaging apparatus to generate the information based on the plurality of images provided as input to the at least one learned model.

15. The computer-implemented method of claim 13, further comprising:
training the at least one learned model based, at least in part on, one or more of shape information, compaction information, contraction information, expansion information, dormant information, and quality information.

16. The computer-implemented method of claim 13, further comprising:
receiving, via the web dashboard, progress information including information describing a condition of an animal from which the fertile ovum was grown; and
retraining the learned model based, at least in part, on the progress information.

17. A non-transitory computer readable medium encoded with a plurality of instructions that, when executed by computer processing circuitry, perform a method comprising:
receiving, from an imaging apparatus, a plurality of images of a fertile ovum captured in time-series;
processing the plurality of images of the fertile ovum received from the imaging apparatus to generate information based on the plurality of images of the fertile ovum, wherein processing the plurality of images comprises performing deep learning analysis to extract a profile line of the fertile ovum in the plurality of images;
providing as input to at least one learned model, the plurality of images of the fertile ovum or the generated information based on the plurality of images, wherein the at least one learned model has been trained to output, based at least in part, on the plurality of images, fertile ovum analysis information describing characteristics of the fertile ovum used to evaluate a quality of fertile ovum; and
displaying, on a web dashboard provided in a web browser, evaluation support information based, at least in part, on the fertile ovum analysis information, wherein the evaluation support information enables a quality evaluator to interact with the web dashboard to modify at least some of the evaluation support information.

18. A computer system for evaluating the quality of a fertile ovum, the computer system comprising:
computer processing circuitry configured to:
receive a plurality of images of a fertile ovum captured in time-series by an imaging apparatus;
process the plurality of images of the fertile ovum received from the imaging apparatus to generate information based on the plurality of images of the fertile ovum, wherein processing the plurality of images comprises performing deep learning analysis to extract a profile line of the fertile ovum in the plurality of images;
provide as input to at least one learned model, the plurality of images of the fertile ovum or the generated information based on the plurality of images of the fertile ovum, wherein the at least one learned model has been trained to output, based at least in part, on the plurality of images, fertile ovum analysis information describing characteristics of the fertile ovum used to evaluate a quality of fertile ovum; and
provide, on a web dashboard provided in a web browser, evaluation support information based, at least in part, on the fertile ovum analysis information, wherein the evaluation support information enables a quality evaluator to interact with the web dashboard to input quality information of the fertile ovum.

19. An imaging processing system for evaluating the quality of a fertile ovum, the image processing system comprising:
an imaging device configured to capture a time-series of images of a fertile ovum, wherein at least a part of the images in the time-series correspond to different developmental stages of the fertile ovum;
a communications interface configured to connect via at least one network to at least one computer; and
at least one storage medium configured to store a plurality of instructions received via the communications interface, wherein the plurality of instructions, when executed by computer processing circuitry, cause the computer processing circuitry to:
control capturing of the time-series of images by the imaging device;
process the time-series of images to generate information based on the time-series of images, wherein processing the time series of images comprises performing deep learning analysis to extract a profile line of the fertile ovum in the time-series of images;
provide the time-series of images or the generated information based on the time-series of images to at least one learned model, wherein the at least one learned model has been trained to output, based at least in part, on the time-series of images, fertile ovum analysis information describing characteristics of the fertile ovum used to evaluate a quality of fertile ovum; and
provide, on a web dashboard provided in a web browser, evaluation support information based, at least in part, on the fertile ovum analysis information, wherein the evaluation support information enables a quality evaluator to interact with the web dashboard to input quality information of the fertile ovum.

20. An imaging processing system for evaluating the quality of a fertile ovum, the image processing system comprising:
an imaging device configured to capture a time-series of images of a fertile ovum, wherein at least a part of the images in the time-series correspond to different developmental stages of the fertile ovum;
a communications interface configured to connect via at least one network to at least one computer; and
at least one storage medium configured to store a plurality of instructions received via the communications interface, wherein the plurality of instructions, when executed by computer processing circuitry, cause the computer processing circuitry to:
process the time-series of images to generate information based on the time-series of images, wherein processing the time-series of images comprises performing deep learning analysis to extract a profile line of the fertile ovum in the time-series of images
provide the time-series of images or the generated information based on the time-series of images to at least one learned model, wherein the at least one learned model has been trained to output, based at least in part, on the time-series of images, fertile ovum analysis information describing characteristics of the fertile ovum used to evaluate a quality of fertile ovum; and
provide, on a web dashboard provided in a web browser, evaluation support information based, at least in part, on the fertile ovum analysis information, wherein the evaluation support information enables a quality evaluator to interact with the web dashboard to input quality information of the fertile ovum.

21. An imaging processing system for evaluating the quality of a fertile ovum, the image processing system comprising:
at least one storage medium configured to store a plurality of instructions that, when executed by computer processing circuitry, cause the computer processing circuitry to:
process the time series of images to generate information based on the time series of images, wherein processing the time series of images comprises performing deep learning analysis to extract a profile line of the fertile ovum in the time series of images;
provide a time-series of images captured by an imaging device or the generated information based on the time-series of images to at least one learned model, wherein the at least one learned model has been trained to output, based at least in part, on the time-series of images, fertile ovum analysis information describing characteristics of the fertile ovum used to evaluate a quality of fertile ovum; and
provide, on a web dashboard provided in a web browser, evaluation support information based, at least in part, on the fertile ovum analysis information, wherein the evaluation support information enables a quality evaluator to interact with the web dashboard to input quality information of the fertile ovum.

* * * * *